(12) United States Patent
Fredenberg et al.

(10) Patent No.: US 11,033,243 B2
(45) Date of Patent: Jun. 15, 2021

(54) IN-LINE X-RAY FOCUSING OPTICS USED FOR MANIPULATION OF X-RAYS IN MEDICAL TRANSMISSION RADIOGRAPHY

(71) Applicant: Prismatic Sensors AB, Stockholm (SE)

(72) Inventors: Erik Fredenberg, Stockholm (SE); Johannes Loberg, Stockholm (SE); Mats Danielsson, Täby (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 16/590,645

(22) Filed: Oct. 2, 2019

(65) Prior Publication Data

US 2020/0330059 A1 Oct. 22, 2020

Related U.S. Application Data

(60) Provisional application No. 62/835,729, filed on Apr. 18, 2019.

(51) Int. Cl.
  *G01N 23/046* (2018.01)
  *A61B 6/00* (2006.01)

(52) U.S. Cl.
  CPC .......... *A61B 6/4241* (2013.01); *A61B 6/4021* (2013.01); *A61B 6/484* (2013.01); *A61B 6/487* (2013.01); *A61B 6/502* (2013.01)

(58) Field of Classification Search
  CPC ..... A61B 6/4021; A61B 6/405; A61B 6/4064; A61B 6/042; A61B 6/42; G02B 21/08;
  (Continued)

(56) References Cited

U.S. PATENT DOCUMENTS 6,472,665 B1 * 10/2002 Ishisaka ................ G01T 1/2018
  250/368
2011/0194674 A1 8/2011 Mukaide et al.
  (Continued)

FOREIGN PATENT DOCUMENTS

EP  3 447 539 A1  2/2019
EP  3 271 898 B1  10/2019
  (Continued)

OTHER PUBLICATIONS

Twengström, William, "High-resoluton biomedical phase-contrast tomography," Doctoral Thesis No. 34, 2018, KTH Royal Institute of Technology, Engineering Sciences Department of Applied Physics.
  (Continued)

*Primary Examiner* — Don K Wong
(74) *Attorney, Agent, or Firm* — Nixon & Vanderhye

(57) ABSTRACT

There is provided an arrangement including an x-ray detector arranged in conjunction with in-line x-ray focusing optics configured for manipulation of x-rays in medical transmission radiography, wherein the in-line x-ray optics includes an array of lenses, in which the lenses cover parts of, or the entire, field of view, and in which the x-ray detector is a photon-counting detector. Furthermore, the x-ray detector is an energy-resolving detector and chromatic aberration of the lens array and/or limited coherence of the source is compensated for by the energy resolution of the energy-resolving detector, and/or the x-ray detector is a depth-resolving detector and chromatic aberration of the lens array and/or limited coherence of the source is compensated for by depth resolution or volumetric resolution in the detector.

29 Claims, 15 Drawing Sheets

(58) Field of Classification Search
CPC .... G02B 21/26; G02B 21/16; G02B 23/2461; G02B 23/2469; G02B 3/0037; G02B 21/0032; G01Q 60/18
See application file for complete search history.

(56) References Cited

U.S. PATENT DOCUMENTS

| | | | |
|---|---|---|---|
| 2015/0055744 | A1 | 2/2015 | Anton et al. |
| 2017/0219503 | A1 | 8/2017 | Vedantham et al. |
| 2017/0261442 | A1 | 9/2017 | Yun et al. |
| 2018/0156742 | A1 | 6/2018 | Cao et al. |
| 2019/0008474 | A1 | 1/2019 | Sjolin et al. |

FOREIGN PATENT DOCUMENTS

| | | |
|---|---|---|
| JP | 2008200357 A | 9/2008 |
| WO | 2008/102632 A1 | 8/2008 |
| WO | 2014187588 A1 | 11/2014 |
| WO | 2018/164621 A1 | 9/2018 |
| WO | 2019/027761 A1 | 2/2019 |

OTHER PUBLICATIONS

Beck et al.; Quantitative x-ray dark-field computed tomography; Physics in Medicine and Biology; Aug. 31, 2010; pp. 5529-5539; vol. 55; IOP Publishing.

Schlomka; Coherent scatter computed tomography: a novel medical imaging technique; Proceedings of SPIE 5030; Medical Imaging 2003; Physics of Medical Imaging; Jun. 5, 2003; pp. 256-265; vol. 5030.

Attwood et al.; X-Rays and Extreme Ultraviolet Radiation; 2016; pp. 67-69, 134, 469 and 578-591.

Pfeiffer; Phase retrieval and differential phase-contrast imaging with low-brilliance X-ray sources; Nature Physics; Apr. 2006; pp. 258-261; vol. 2; Nature Publishing Group.

Scherer; Grating-Based X-Ray Phase-Contrast Mammography; Springer; 2016.

Michel; On a dark-field signal generated by micrometer-sized calcifications in phase-contrast mammography; Physics in Medicine and Biology; 2013; pp. 2713-2732; vol. 58; IOP Publishing.

Gromann; In-vivo X-ray Dark-Field Chest Radiography of a Pig; Science Reports; 2017; pp. 1-7; vol. 7.

Jensen et al.; Directional x-ray dark-field imaging; Physics in Medicine and Biology; 2010; pp. 3317-3323; vol. 55.

Hubbell; Summary of existing information on the incoherent scattering of photons, particularly on the validity of the use of the incoherent scattering function; Radiation Physics and Chemistry; Jul. 1997; pp. 113-124; vol. 50, No. 1.

Schlomka et al.; Experimental feasibility study of energy-resolved fan-beam coherent scatter computed tomography; Proceedings of the SPIE; Oct. 2004; pp. 410-423; vol. 5535.

Cozzini et al.; Energy dispersive X-ray diffraction spectral resolution considerations for security screening applications; IEEE Nuclear Science Symposuim & Medical Imaging Conference; Oct. 2010; pp. 3873-3876.

Nisar et al.; Coherent scatter x-ray imaging of plastic/water phantoms; Proceedings of the SPIE; Oct. 2004; pp. 445-453; vol. 5578.

Snigirev et al.; A compound refractive lens for focusing high-energy X-rays; Nature; Nov. 7, 1996; pp. 49-51; vol. 384.

Snigirev et al.; High energy X-ray nanofocusing by silicon planar lenses; Journal of Physics, Conference Series 186; Sep. 2009.

Fredenberg et al.; A Tunable Energy Filter forMedical X-Ray Imaging; X-Ray Optics and Instrumentation; Oct. 2008; vol. 2008.

Fredenberg et al.; A low-absorption x-ray energy filter for small-scale applications; Optics Express; Jul. 6, 2009; pp. 11388-11398; vol. 17, No. 14.

Nillius et al.; Large-aperture focusing of high-energy x rays with a rolled polyimide film; Optic Letters; Feb. 15, 2011; pp. 555-557; vol. 36, No. 4.

Mi et al.; Fabrication of circular sawtooth gratings using focused UV lithography; Journal of Micromechanics and Microengineenng; Jan. 20, 2016; vol. 26.

Mi et al.; A stacked prism lens concept for next-generation hard X-ray telescopes; Nature Astronomy; Sep. 2019; pp. 867-872; vol. 3.

Fredenberg et al.; An efficient pre-object collimator based on an x-ray lens; Medical Physics; Feb. 2009; pp. 626-633; vol. 36, No. 2.

Persson; Spectral Computed Tomography with a Photon-Counting Silicon-Strip Detector; KTH Royal Institute of Technology, 2016; May 2016; Stockholm, Sweden.

Pagot et al.; Quantitative comparison between two phase contrast techniques: diffraction enhanced imaging and phase propagation imaging; Physics in Medicine and Biology; Feb. 2, 2005; pp. 709-724; vol. 50.

Thomas; Optimized centroid computing in a Shack-Hartmann sensor; Proceedings of the SPIE; Oct. 2004; pp. 1238-1246; vol. 5490.

Zanette et al.; Speckle-Based X-Ray Phase-Contrast and Dark-Field Imaging with a Laboratory Source; Physical Review Letters; Jun. 27, 2014; vol. 112, 25903.

Bech et al.; In-vivo dark-field and phase-contrast x-ray imaging; Scientific Reports; Nov. 13, 2013; vol. 3, 3209.

International Search Report, dated Jan. 17, 2020, from corresponding PCT Application No. PCT/SE2019/050950.

Wang et al., "Material separation in x-ray CT with energy resolved photon-counting detectors," Med. Phys., Mar. 2011, vol. 38, No. 3, pp. 1534-1546.

Lundqvist et al., "Evaluation of a Photon-Counting X-Ray Imaging System," IEEE transactions of nuclear science, 2001, vol. 48, No. 4, pp. 1530-1536.

\* cited by examiner

IN-LINE X-RAY FOCUSING OPTICS USED FOR MANIPULATION OF X-RAYS IN MEDICAL TRANSMISSION RADIOGRAPHY

The project leading to this application has received funding from the European Union's Horizon 2020 research and innovation programme under grant agreement No 830294.

TECHNICAL FIELD

The proposed technology relates to medical x-ray imaging in general and particularly to photon-counting x-ray imaging and arrangements, methods and systems for supporting and/or enabling such imaging. The invention further relates to phase-contrast and dark-field imaging methods for medical diagnosis.

BACKGROUND

Clinical x-ray imaging is for the most part based on attenuation contrast. X-rays transmitted through an object will attenuate according to Beer's law $I=I_0 \exp(-\int\mu(z) dz)$, where $\mu$ is the linear attenuation coefficient which depends on the elemental decomposition of the material. The relative differences in attenuation between different materials in the body provide the contrast in an x-ray image. Interfaces between dense tissues and soft tissues in the body provide excellent contrast, but attenuation-based imaging is intrinsically limited in its capability to differentiate tissues with small relative attenuation differences such as between blood vessels and soft tissues. One challenge is that low-contrast imaging tasks are compounded by scattering in the object. Further, attenuation of x-rays is basically a function of electron density and atomic number; other properties such as on a molecular level cannot be detected. These inherent limitations of attenuation-based contrast reduce the ability of state-of-the-art x-ray imaging systems to detect or characterize many important pathological conditions such as cancers and stroke.

X-ray imaging techniques to characterize objects on material properties other than attenuation, such as x-ray phase-contrast and dark-field imaging, are emerging. These methods have been available for research purposes for decades, but stringent requirements on source coherence have limited clinical applications. New techniques with less strict demands on source coherence have been demonstrated (1), but clinical implementation is still facing a number of challenges. (2)

X-Ray Scattering

X-rays, which are attenuated in the body, are either absorbed or scattered. The basis for attenuation imaging is that detected photons have traversed the object in a straight path and scattered x-rays from other parts of the object violate this assumption (unless the scatter angle is very small). The scatter-to-primary ratio (SPR) is used to quantify the ratio between detected scattered and primary photons. The contrast-to-noise ratio (CNR) is reduced by scatter with a factor of $1/\sqrt{1+SPR}$.

Medical x-ray imaging systems commonly use anti-scatter grids to reduce the SPR and to improve CNR. Absorbing lamella prevent incident scattered photons outside of a narrow angle-span to reach the detector. The drawback of anti-scatter grids is that a portion of primary photons are shadowed, and the geometrical efficiency drops, which introduces a tradeoff between efficient scatter rejection and dose efficiency. In addition, reducing the acceptance angle by way of increasing lamella height poses higher demand on the manufacturing process and requires careful alignment with the source.

Phase-Contrast Imaging

Phase contrast has been demonstrated to increase morphological delineation of different soft tissues which exhibit very low contrast in traditional attenuation-based imaging. (2) Phase-contrast imaging is based on coherent scattering, which gives rise to non-random phase changes. (3, 4) Coherent scattering dominates over incoherent scattering for small scattering angles. (5)

X-rays refract and undergo phase shifts when propagating through material interfaces. The complex index of refraction is used to characterize different materials in terms of their attenuation and phase change properties, and is defined as $$n=1-\delta+i\beta. \tag{1}$$

The real part of the refractive index relates to the phase shift. The decrement from unity $\delta$ is very small and typically in the order of magnitude of $10^{-5}$ to $10^{-7}$ for hard x-rays in the diagnostic range. $\beta$ is related to the linear attenuation of the material: $\mu=4\pi\beta/\lambda$ (6).

A plane wave propagating through an object along the positive z-axis can be treated as a product of three exponential terms: $E=E_0 \exp(ikz)\times\exp(-ik\delta z)\times\exp(-\mu z/2)$, where the first term describes propagation through vacuum, the second term accounts for phase changes and the third term accounts for attenuation (6) The total phase shift through the object is (3): $\Phi(x, y)=-2\pi/\lambda\times\int\delta(x, y, z)dz$. Attenuation-based imaging measures the intensity: $|E|^2=|E_0|^2\times\exp(-uz)$, and phase information is therefore lost ("the phase problem").

To recover the phase of the transmitted wave, there are several methods described in the literature, including speckle-based tracking (1), propagation-based methods (3), and grating-based methods, such as the Talbot-Lau interferometer (3). In propagation-based imaging, phase variations are detected by varying the detector distance to the object. The phase signal can be shown to be proportional to the second derivative of the phase signal ($\nabla^2\Phi$) and therefore gives a strong signal at high spatial frequencies (3). Propagation-based methods have been used in biomedical applications, but the acquisition time for a single projection can be several minutes and tomographic imaging can take hours, which poses challenges for clinical applications (3).

Another option for solving the phase problem is grating-based imaging, such as the Talbot-Lau interferometer setup (7). In Talbot-Lau setups, a phase grating (G1) and an analyzer grating (G2) are arranged a distance apart equal to the first Talbot distance. G1 creates an interference pattern at G2, which is perturbed by a phase gradient in the object. G2 has a high-frequency pitch and is scanned to analyze the interference pattern with a detector of relatively low resolution. A Talbot-Lau setup can be implemented with a source grating G0 with a pitch chosen such that spatial coherence is improved but at a higher photon economy compared to a single slit (8).

US 2017/0219503 relates to an x-ray phase contrast imaging apparatus and method of operating the same. The apparatus passes x-rays generated by an x-ray source through, in succession, a source grating, an object of interest, a phase grating, and an analyzer grating. The x-ray source, the source grating, the phase grating, and the analyzer grating move as a single entity relative to an object of interest. The phase grating and the analyzer grating remain in fixed relative location and fixed relative orientation with respect to one another. The detected x-rays are converted to a time sequence of electrical signals (32).

Dark-Field Imaging

The detected signal in Talbot-Lau setups allows for measuring phase contrast and attenuation in a single acquisition, but also to acquire a dark-field image. The contrast in dark-field imaging is provided by small-angle scattering (5, 8), which depends on the molecular structure of the object. Dark-field imaging can improve contrast of microstructures such as fibers, fine structures of bone, micro-calcifications (9), and micron-sized alveoli destruction and densification in the lung (2,10,11).

Small-angle scattering is an umbrella term for several different physical phenomena. The Klein-Nishina formula, which describes incoherent Compton scattering, overestimates the forward-peaked scattering component (12,13), and small-angle scattering has been shown to be dominated by coherent scattering (14,15), which is strongly forward-peaked. Adopting the formalism in Ref. (4), the total contribution of small-angle scattering can be treated as having an approximately Gaussian angular distribution for narrow scattering angles. A beam traversing a non-absorbing object slice results in a scattered intensity:

$$A_1(\theta) = \frac{1}{\sigma_1 \sqrt{2\pi}} \times \exp - \frac{\theta^2}{2\sigma_1^2}, \quad (2)$$

where $\sigma$ is material and structure dependent. Broadening from N stacked object slices can then be described as the convolution $A(\theta)=A_1(\theta)*A_2(\theta)* \ldots *A_N(\theta)$ and the width of this distribution is given by $\sigma^2=\Sigma_{i=1}^{N}\sigma_i^2$. This broadening can be described by the linear diffusion coefficient (E), defined in terms of a as:

$$\sigma^2=\int\varepsilon(z)dz. \quad (3)$$

Tomographic images can be reconstructed by back-projection of $\varepsilon$.

Grating-based imaging is associated with several challenges that have hitherto hampered clinical introduction. The mechanical translation of G2 severely impacts the acquisition time, which can be as long as 40 s for a single projection in large (32×35 cm²) field-of-view setups (10). Such lengthy exposure times would lead to severe motion artifacts in a clinical setting, due to e.g. breathing. In addition, the photon economy and dose efficiency are reduced by absorption in the gratings, which leads to higher dose and longer exposure times or higher tube load as would be the case without a grating. Further, even though spatial coherence can be improved by G0, temporal coherence is still limited by a polychromatic source.

X-Ray Optics

Some of the challenges encountered in absorption-based, phase-contrast, and dark-field configurations can be mitigated by using x-ray optics to manipulate the x-ray beam. X-ray optics are based on the complex refractive index n as defined in Eq. (1). The decrement from unity ($\delta$) of the real part of n determines the refraction angle and is close to zero for x-rays. Further, $\delta$ depends on material composition and is proportional to the real part of the atomic scattering factor ($f_1^0(E)$, where E is photon energy) and to the atomic density and inversely proportional to the square of the photon energy. In general, $f_1^0(E)$ decreases asymptotically to the atomic number of the material and is approximately constant for photon energies above 20 keV (6).

The weak refraction is one of the main challenges in designing x-ray optics. Grazing-incidence-based optics, such as the Wolter type 1 optics, instead utilize the critical angle for total external reflection (approximately equal to $\sqrt{2\delta}$) by a series of layered mirrors. The mirrors are placed near parallel to the incident beam, so multiple reflections focus the beam. These types of optics have long focal lengths and are limited by strict engineering tolerances, small field-of-views, and a narrow functional energy range.

Refraction-based lenses allow for shorter focal lengths at hard x-ray energies; biconcave lenses have focal lengths of f=R/2$\delta$, where R is the radius (equal on both sides). Manufacturing is facilitated (increased R) by so-called compound refractive lenses, in which N individual lenses are stacked along the optical axis to reduce the focal length by a factor of N (16). For instance, a series of compound lenses have been tested for hard x-rays, in which each lens had a radius corresponding to a focal length of 10 cm at a specific energy (ranging from 10 keV to 80 keV with 5 keV increments). At each energy interval, the focal spot width at half maximum was less than 200 nm (17). One drawback of all refractive optics is that transmission is rapidly reduced towards the periphery of the concave lenses, and low-Z materials, such as silicon or beryllium, is preferentially used to increase transmission.

Another avenue to increase transmission is to remove lens material corresponding to a phase shift of integer steps of $2\pi$, resulting in diffraction-based optics, such as Fresnel zone plates and Fresnel lenses (6). Manufacturing of these lenses is, however, challenging because of fine structures and high aspect ratios. The focal lengths of these optics are therefore typically in the range of several meters and are impractical for use in medical imaging.

The so-called multi-prism lens comprises two rows of prisms at an angle in relation to the optical axis (18). The projection of this arrangement approximates a parabola and therefore works as a refractive lens, but manufacturing is facilitated compared to a conventional concave lens. As for all refractive lenses, the Gaussian transmission profile limits the usable aperture, and a diffraction-based version, the so-called prism-array lens, can be realized by exchanging each prism for a column of smaller prisms (19). The aperture can thus be made substantially larger. Because of the relatively simple structures (prisms), complexity is lower than would be the case for a Fresnel lens, which enables shorter focal lengths in practice. Prism-type lenses were at first one dimensional but has evolved into two-dimensional arrangements (20). The most recent prism-type lens is the stacked prism lens with demonstrated ease of mass production (21,22,23). FIG. 1a) shows a 3D rendering of the lens, wherein stacks of discs with an increasing number of prisms toward the periphery accomplish the desired focusing effect. FIG. 1b) shows a cross section of one disc with the embedded circular prismatic rings. The principle of the stacked prism lens, consisting of identical prisms that refract, and therefore focus, x-rays, is shown in FIG. 1c). Notation in FIG. 1: d is the displacement between two adjacent prism columns, h is the prism height, b is the prism base, and $\theta$ is the angle subtended by the prism height, i.e. $\tan^{-1}$(h/b). The lens focuses in two dimensions and the focal length can be less than 0.1 m. This type of lens has been investigated for use in x-ray telescopes and can be deployed in arrays of very flexible size and focal lengths less than 10 cm (23).

There are a few examples of medical x-ray imaging applications based on x-ray optics in the prior art. One-dimensional prism-type lenses have been investigated for spectral shaping as an alternative to attenuation filtering of x-ray spectra (18,19), and for efficient collimation (24). These types of fan-beam arrangements are well suited for some scanning x-ray imaging systems that are intrinsically one-dimensional but are suboptimal for two-dimensional systems.

US2015/0055744A1 describes an x-ray lens grating disposed between the phase grating and the x-ray detector for grating-based phase-contrast imaging (25). This arrangement could improve photon economy but does not present a solution to the long acquisition times and loss of dose efficiency inherent to translating grating-based systems.

WO2014/187588A1 describes a phase-contrast imaging configuration in which an in-line lens array is positioned upstream of the detector (26). JP2008200357A describes a configuration similar in purpose and execution (27). Perturbations by a phase gradient in the object could be measured in analogue with a Shack-Hartmann wave front sensor for optical wave lengths, which would allow for concurrent acquisitions of attenuation and phase-contrast images. However, neither WO2014/187588A1 nor JP2008200357A describes any method to measure the dark-field signal of an object. Further, the limited coherence of realistic medical x-ray imaging configurations is also not addressed by the method in WO2014/187588A1 or in JP2008200357A. In other words, chromatic aberrations of the x-ray optics will blur the focal point of a polychromatic x-ray spectrum, as will the finite source size.

Photon-Counting Detectors

Photon-counting detectors (PCDs) record individual photon interactions in the detector and can eliminate electronic noise, which allows for smaller detector elements while maintaining the signal-to-noise ratio. PCDs can also provide spectral information on photon interactions by measuring the corresponding pulse height. Finally, photon-counting silicon strip detectors can be made to locate the depth of interaction in the material (28).

SUMMARY

It is a general object to support and/or enable photon-counting x-ray imaging.

It is a specific object to provide an improved arrangement comprising an x-ray detector arranged in conjunction with in-line x-ray focusing optics configured for manipulation of x-rays.

Another object is to provide an x-ray imaging system and/or a system for medical x-ray imaging comprising such an arrangement.

These and other objects are met by embodiments of the proposed technology.

According to a first aspect, there is provided an arrangement comprising an x-ray detector arranged in conjunction with in-line x-ray focusing optics configured for manipulation of x-rays in medical transmission radiography, wherein the in-line x-ray optics comprise an array of lenses, in which the lenses cover parts of, or the entire, field of view, and in which the x-ray detector is a photon-counting detector. Furthermore, the x-ray detector is an energy-resolving detector and chromatic aberration of the lens array and/or limited coherence of the source is compensated for by the energy resolution of the energy-resolving detector, and/or the x-ray detector is a depth-resolving detector and chromatic aberration of the lens array and/or limited coherence of the source is compensated for by depth resolution or volumetric resolution in the detector.

According to a second aspect, there is provided an x-ray imaging system and/or a system for medical x-ray imaging comprising an arrangement according to the first aspect.

In this way, it is possible to improve detection and diagnosis in medical x-ray imaging, e.g. by enhancing phase-contrast information, enhancing dark-field information, and/or efficiently removing Compton-scattered photons, Other advantages will be appreciated when reading the following detailed description of non-limiting embodiment of the invention.

BRIEF DESCRIPTION OF DRAWINGS

The embodiments, together with further objects and advantages thereof, may best be understood by making reference to the following description taken together with the accompanying drawings, in which.

DETAILED DESCRIPTION

Figure 1:
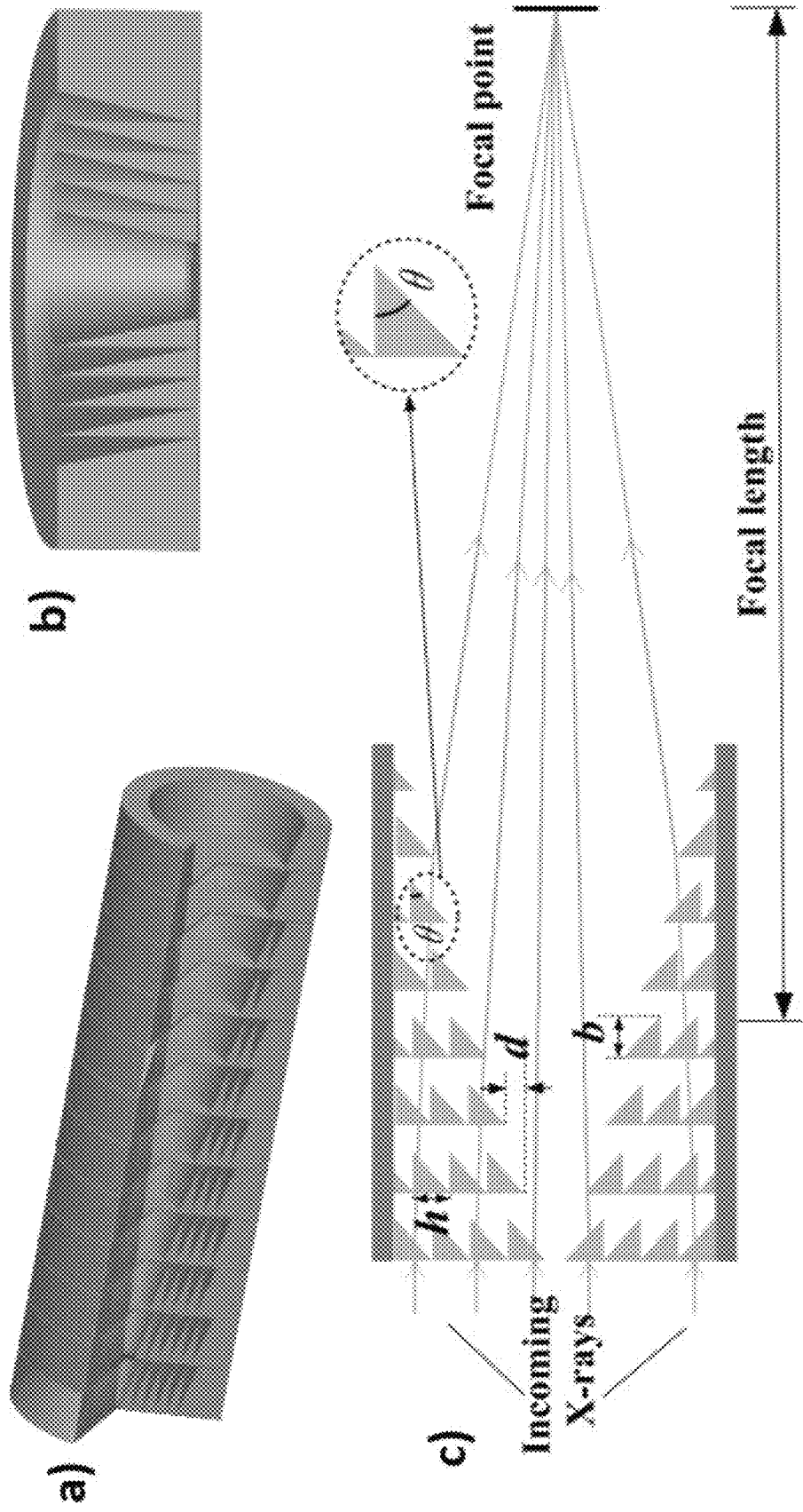
FIG. 1 is a schematic diagram illustrating an example of a refractive x-ray lens, a plurality of which can be arranged to form a lens-array.

Basically, the present invention relates to an x-ray imaging setup, where an in-line lens array is used to manipulate and divert the incoming flux of photons incident on a photon-counting x-ray detector.

In the following, reference will be made to an arrangement, which should be seen as any physical arrangement, apparatus or system that is configurable for x-ray detection and/or imaging purposes.

According to a first aspect, the proposed technology provides an arrangement comprising an x-ray detector arranged in conjunction with in-line x-ray focusing optics configured for manipulation of x-rays in medical transmission radiography, wherein the in-line x-ray optics comprises an array of lenses, in which the lenses cover parts of, or the entire, field of view, and in which the x-ray detector is a photon-counting detector. Furthermore, the x-ray detector is an energy-resolving detector and chromatic aberration of the lens array and/or limited coherence of the source is compensated for by the energy resolution of the energy-resolving detector, and/or the x-ray detector is a depth-resolving detector and chromatic aberration of the lens array and/or limited coherence of the source is compensated for by depth resolution or volumetric resolution in the x-ray detector.

For example, the energy and/or depth resolution of the photon-counting detector may be used to sort photons into categories, which are treated differently depending on the energy and/or depth of interaction. In an example configuration, (optimal) weighting of the photons may be applied such that photons carrying more information are assigned a higher weight compared to photons carrying less information. The information referred to here may be, for instance, contrast information; if it is desired to increase the contrast caused by the photo-electric effect with an energy dependence approximately inversely proportional to the energy cubed ($E^{-3}$), lower x-ray energies can be assigned a relatively higher weight, whereas if it is desired to increase the contrast caused by any other interaction effect, such as Compton scattering with an approximately constant energy dependence ($E^0$) or phase shift with an energy dependence approximately inversely proportional to the energy squared ($E^2$), another weighting scheme might be applied. Nevertheless, the information carried by photons may also have an energy dependence caused by phenomena other than interaction effects, such as technical or physical constraints by the imaging setup. For instance, if the imaging setup is designed to have optimal performance at a certain x-ray energy or interval of x-ray energies, photons of these energies may be assigned a relatively higher weight. The same reasoning applies to the depth of interaction; if the imaging setup is designed for photons to interact at a certain depth or interval of depths in the detector, photons interacting at these depths may be assigned a relatively higher weight.

In other words, the arrangement or system may be configured to sort photons by using the energy and/or depth resolution of the photon-counting detector, and treating the photons differently depending on the energy and/or depth of interaction. By way of example, the arrangement or system may be configured to assign higher weights to photons carrying more information and relatively lower weights to photons carrying less information. This may be very useful for the subsequent image processing and/or reconstruction process(es). In this context, it should be understood that suitable processing circuitry such as analog and/or digital processing circuitry and/or processor-memory implementations may be used and configured to perform the sorting and/or the weighting of photons.

With an energy-resolving photon-counting detector, each count is related to the incident photon energy. In addition, photon-counting detectors enable volumetric resolution so that each count is related to the depth of interaction of the incident photon.

By way of example, the relative amount of counts outside of the focal spot may be low near the optimal energy of the lens and low levels of electronic noise may therefore be necessary to extract the signal, which is enabled by the photon-counting detector in the present invention. Moreover, energy and depth resolution of the photon-counting detector can be used to discriminate against primary (non-scattered) photons outside of the optimal energy at a certain detector depth. Without energy- or depth-resolving capabilities, the focal spot blur caused by small-angle scattering may be polluted by non-focused primary photons.

In a particular, non-limiting example the arrangement may be configured to separate primary photons from scattered photons such that primary photons, which are parallel or near parallel, are concentrated to a focus, whereas scattered photons with a wider angular distribution are not concentrated to a focus.

For example, the x-ray detector may be a pixelated detector and the separation between primary and scattered photons may be conducted with the pixelated detector, said detector having two or more pixels covering each lens in the lens array.

By way of example, scattered photons may be blocked by means of an anti-scatter grid in addition to the lens array.

Alternatively, scattered photons may be blocked by means of a pin hole or a slit upstream of the x-ray detector.

Optionally, the arrangement may be configured for operation with raytracing methods used in conjunction with energy and/or depth resolution in the x-ray detector to increase spatial resolution of the arrangement.

In a particular example, the arrangement may be configured to estimate or enable estimation of the local phase gradient of the imaged object in one or two dimensions at each lens from the detected location of the focal spot relative to the optical axis of the lens.

Alternatively, or as a complement, the arrangement may be configured to obtain or enable the obtaining of information on small-angle scattering in the object from the broadening of the focal spot or from the total signal outside of the focal spot peak.

For example, the arrangement may be configured to determine or enable determination of the location and/or size of the focal spot of each lens by scanning a grating or a number of pin holes in front of the x-ray detector.

By way of example, the x-ray detector may be a high-resolution detector and the arrangement may be configured to determine or enable determination of the location and/or size of the focal spot of each lens by detecting the signal with the high-resolution detector, said detector having a resolution higher than the deviation of the focal spot from its nominal size and position.

As an example, the arrangement may be configured to determine or enable determination of the location and/or size of the focal spot to a higher resolution than the x-ray detector, where two or more detector elements of the x-ray detector sample the distribution of focused photons reaching the x-ray detector.

For example, the arrangement may comprise a grating or a number of pin holes placed in front of the source, such that each lens in the lens array is operable for imaging a number of spots.

For illustrative purposes, it should be understood that the arrangement may be configured for breast imaging, computed tomography and/or fluoroscopic imaging.

Optionally, the arrangement may be configured to simultaneously acquire at least two (possibly all) of transmission, phase-contrast and dark-field images.

As an example, the lens array may be configured for focusing in one dimension so that the focus is a line.

Alternatively, the lens array may be configured for focusing in two dimensions so that the focus is a spot.

By way of example, the lens array may be placed between the object and the x-ray detector. Alternatively, the lens array may be placed between the source and the object.

According to a second aspect, there is provided an x-ray imaging system and/or a system for medical x-ray imaging comprising an arrangement according to the first aspect.

By way of example, the x-ray detector may be an energy-resolving detector and the system may be configured to decompose the focus into energy-resolved components.

Alternatively, or as a complement, the x-ray detector may be a depth-resolving detector and the system may be configured to compensate for the chromatic aberration by using the depth resolution or volumetric resolution of the x-ray detector, either independently or in conjunction with energy resolution of the x-ray detector.

Optionally, the system is configured for performing ray-tracing in conjunction with energy and/or depth resolution in the x-ray detector to increase spatial resolution.

In an exemplary aspect, the method and configuration proposed in this invention aims to improve medical x-ray imaging systems, particularly mammographic and x-ray computed tomography systems, using novel applications of in-line x-ray optics combined with photon-counting detectors. As mentioned, an exemplary embodiment realizes simultaneous acquisition of two or more of transmission, phase-contrast, and dark-field images.

By way of example, the setup enables separating primary from scattered photons to improve the scatter-to-primary ration and hence the contrast. The setup further enables phase-contrast and dark-field imaging without many of the drawbacks of the prior art.

In the following, the proposed technology will be described with reference to non-limiting examples.

Figure 2:
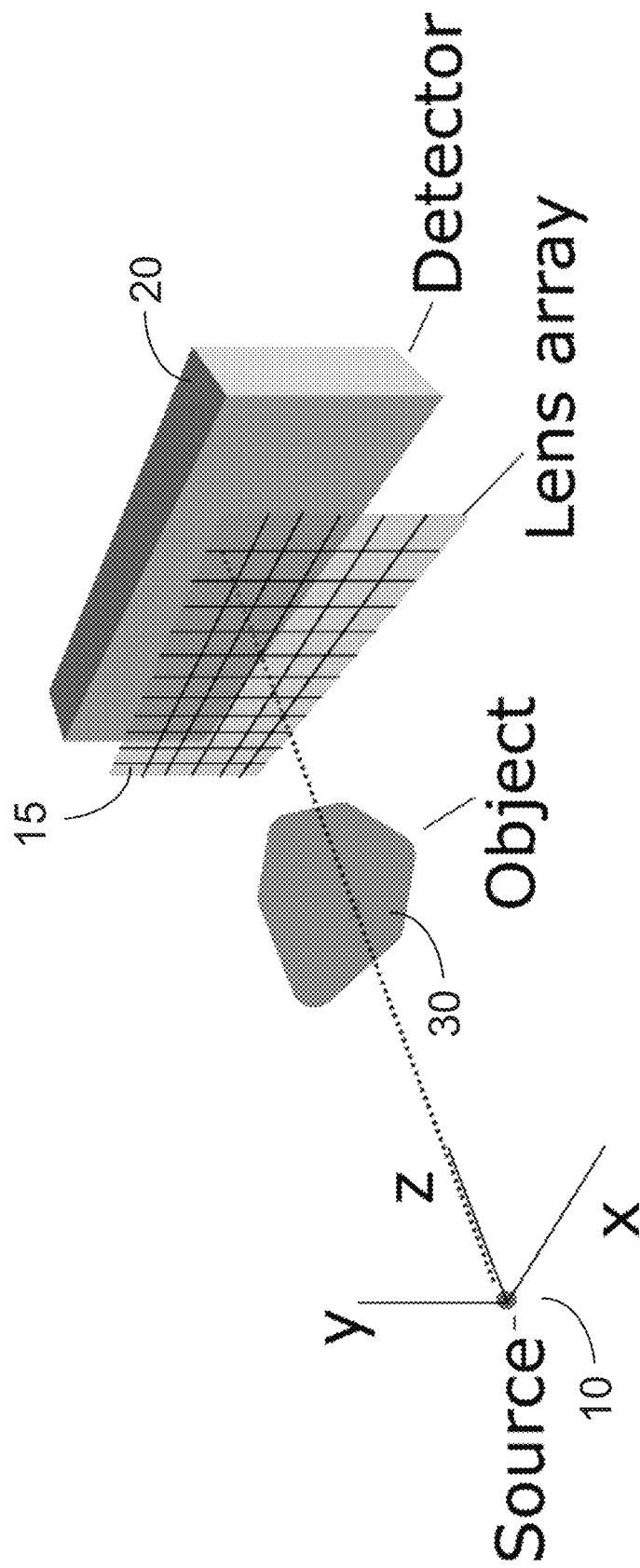
FIG. 2 is a schematic diagram illustrating one embodiment of the arrangement of the in-line lens array relative source, object and detector.

A principal positioning of the in-line x-ray optics or lens-array 15 is schematically shown in FIG. 2. In this geometry, the photons propagate close to the z direction, while the in-line lens array is arranged orthogonal to z axis. In this example, the lens array 15 is composed of lenslets, each focusing x-rays in an energy range appropriate for clinical imaging. FIG. 2 shows the lens array 15 placed between the object 30 and the x-ray detector 20, but it is also conceivable to place it upstream of the object, i.e., between the source 10 and the object 30. The lens array 15 preferentially comprises a prism-type lens or another type of refractive lens, which focuses incident photons in one or two dimensions, i.e., to a line focus or to a spot focus. The photon-counting x-ray detector 20, which is used in conjunction with the lens array 15, compensates for the chromatic behavior present in x-ray lenses and renders the setup more efficient, as described below. The essential features of the photon-counting detector 20 that enables compensating for the chromatic behavior of the lens array include one or several of the following:

Energy resolving capability.

Volumetric spatial resolution, i.e. the x-ray detector can resolve the location of photon interactions in three dimensions.

High spatial resolution in the transverse plane, smaller than the aperture of each individual lenslet.

Negligible or non-existent readout noise.

An incident x-ray wave front on a lens will ideally be focused to one focal point. Due to the chromatic behavior of a refractive lens, the focal point will, however, be finite in size and smeared along the optical axis for a polychromatic x-ray spectrum, such as an x-ray spectrum used in clinical settings today. A conventional x-ray detector will detect the superposition of all the focal spots for all the energies in the spectrum and will not be able to resolve the exact position of the focal spot, as illustrated in FIG. 3a), wherein the incident polychromatic x-rays are focused according to their energies. Shorter wavelengths are depicted as lines with closer spacing and have a longer focal length compared to longer wavelengths, depicted with longer spacing between lines.

Figure 3:
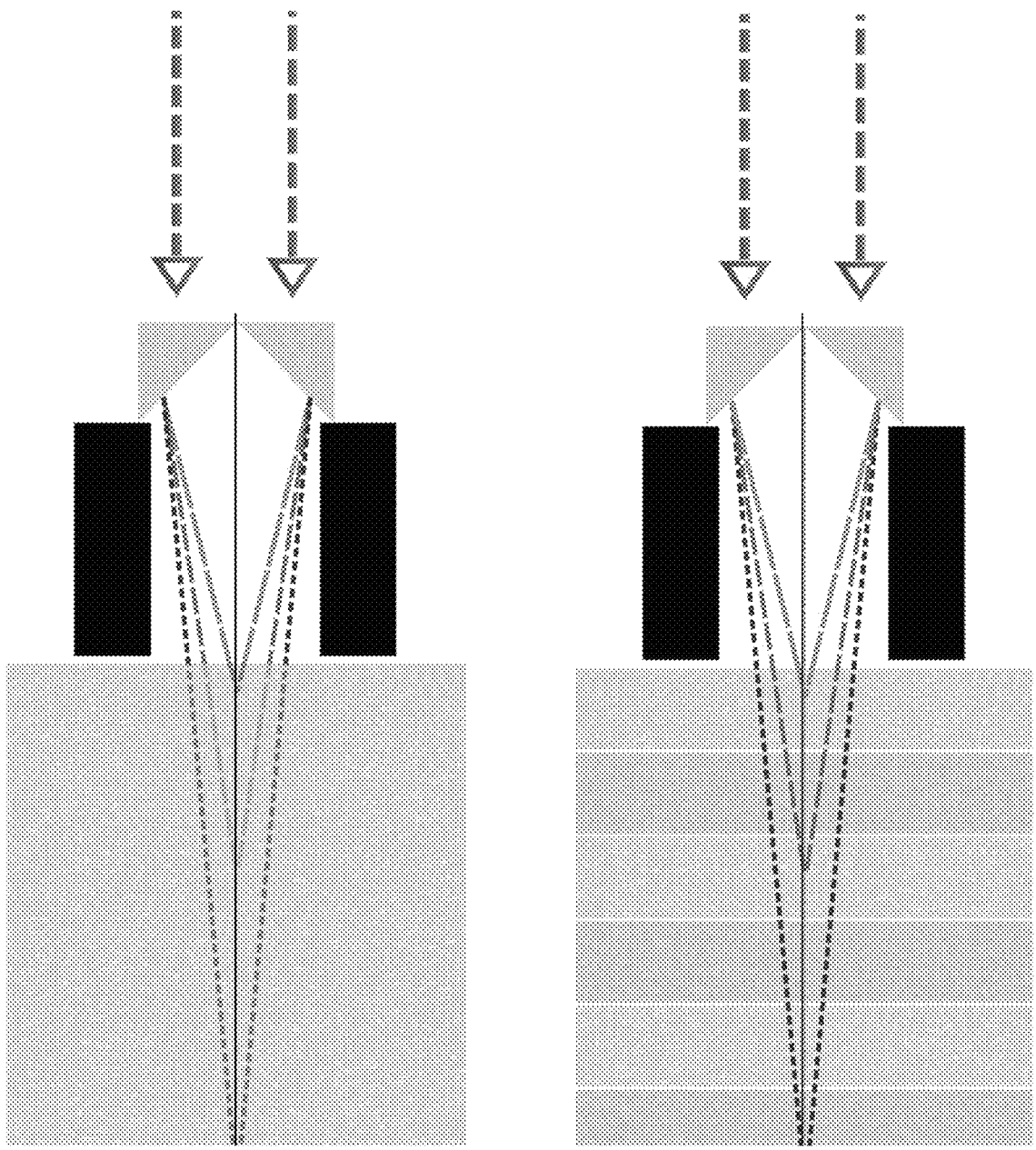
FIG. 3 is a schematic diagram illustrating the chromatic aberration effect in a single lens placed in-line with a detector and the resulting focal spot blurring.

To accurately resolve the focal spot and characterize the focusing of the lens, the invention uses the energy resolution of the photon-counting detector to decompose the smeared focal spot into its spectral components; by relating each detected photon count to its energy, it is possible to decompose the smeared focal spot into its spectral components and reduce the blurring effect. The invention also provides a way to further compensate for the chromatic aberration by using the volumetric resolution of the detector, either independently or in conjunction with the energy resolution of the detector. As principally shown in FIG. 3b), the focal length of the lens varies with photon energy (approximately as $E^2$ for refractive lenses) and for a polychromatic beam it does not coincide with a particular plane in the detector. By detecting the depth of interaction, the invention enables accurate positioning of the focal spot as a function of photon energy to anywhere in the detector. The detector is divided into depth segments in FIG. 3, representing the pixel size along the beam direction.

The described setup enables separating primary photons from scattered photons to improve the contrast in x-ray imaging. Primary photons incident on the lens array are parallel or near parallel and will therefore be focused towards a high-intensity spot on the detector. Scattered photons can, on the other hand, originate from anywhere in the object volume and will therefore exhibit a wide angular distribution. Hence, scattered photons will not be focused to any one spot on the detector but will be spread out with low intensity over the detector surface. Conventional detectors are often limited in spatial resolution, but a high-resolution photon-counting detector can detect the high-intensity focal spot and reject low-intensity areas outside of the focal spot as scatter. The spatial resolution in such a setup will primarily be limited by the size of the lens aperture and not by the detector pixel size as illustrated schematically in FIG. 4a). In this illustrative example, all incident photons reaching the lens are focused to a point, so that the resolution of the final image is limited by the lens aperture rather than by the pixel size.

However, the spatial resolution can be improved by raytracing methods, which are feasible with a photon-counting detector that has both volumetric and energy resolution, as further illustrated in FIG. 4b). Depicted in the left panel of the image, a photon is detected and identified by the coordinates of interaction and its energy. The optical axis and the nominal focal spot for that energy are shown through the center of the lens. In the right panel of FIG. 4b), raytracing is used to locate the coordinates of the photon before it was focused by the lens. If the energy of the impinging photon is detected, the corresponding nominal focal length of the lens can be determined, for instance, from previous calibration measurements, or from the same measurement after a centroid calculation has been carried out. The three spatial coordinates of the detected photon can be used to estimate the trajectory of the photon through the lens. For an ideal thin lens, the photon path can be traced through a simple geometrical model, where the photon can be assumed to have passed through the path between the detected point of interaction and the estimated focal point. This path can be raytraced backwards through the lens to provide spatial information on the original trajectory of the photon.

Figure 5:
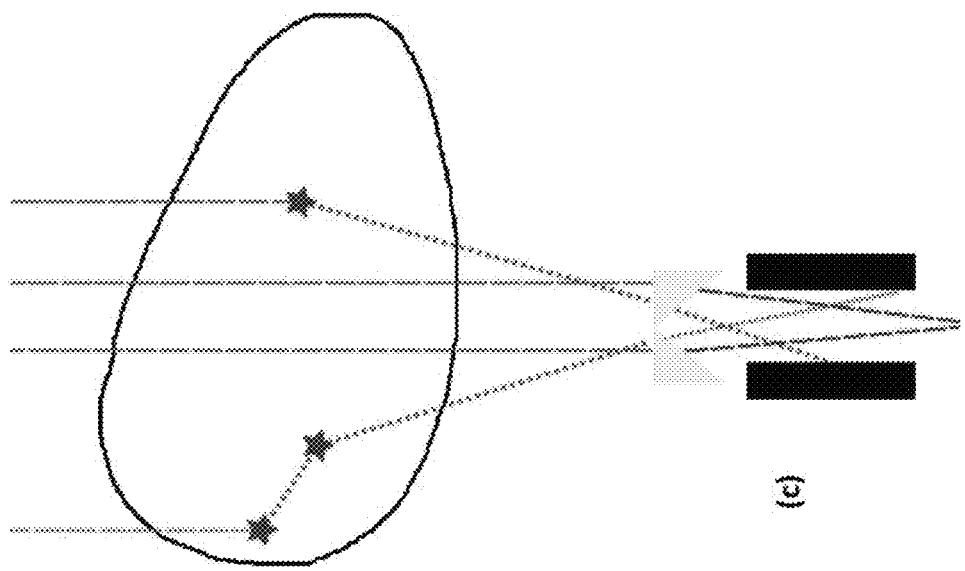
FIG. 5 is a schematic diagram illustrating an example of how primary photons and scattered photons can be discriminated with the lens-array, and how the geometric efficiency associated with a grid can benefit from the use of an upstream lens-array.
Figure 5:
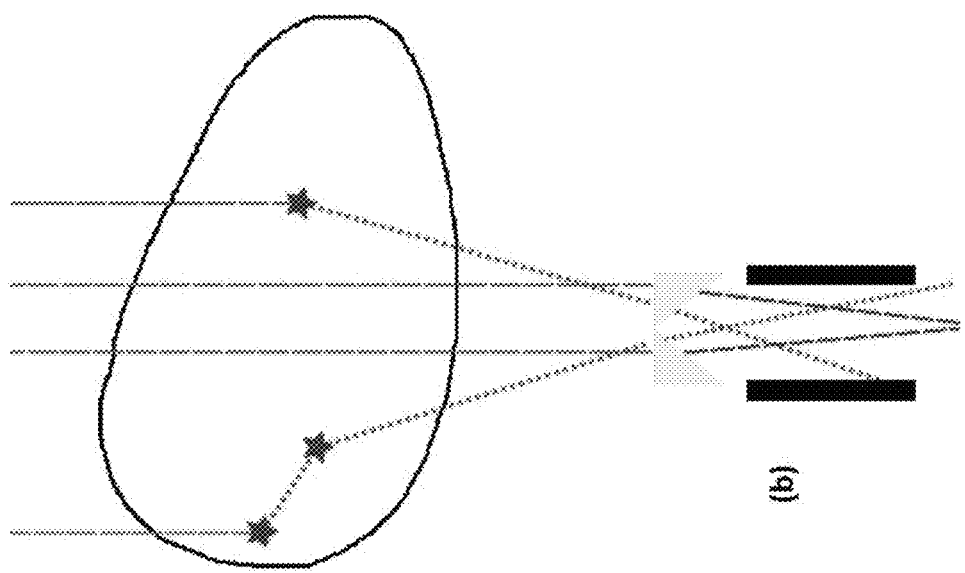
Figure 5:
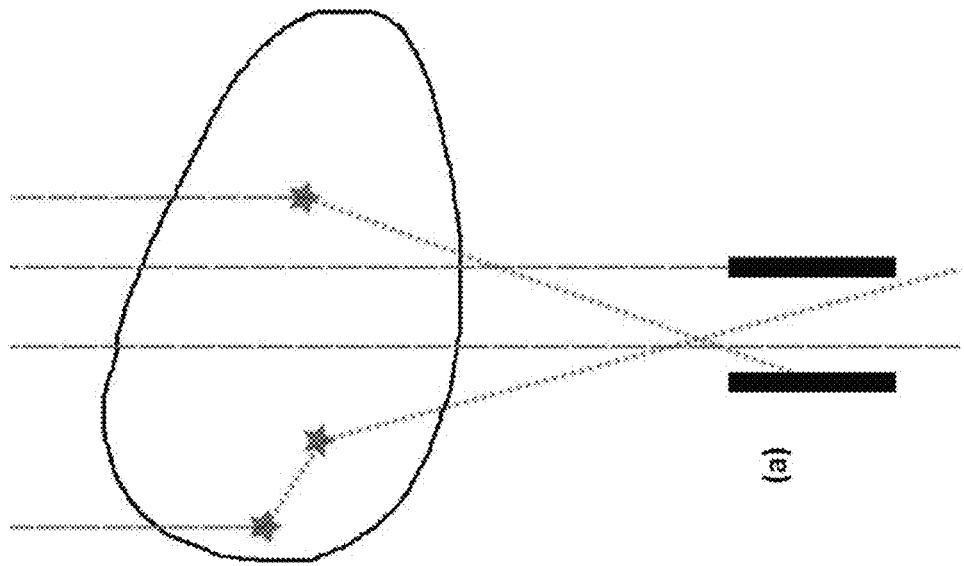

The described application of the lens array combined with a photon-counting detector to reject object scattering is more efficient than conventional anti-scatter grids because the geometric efficiency is not limited by any lamellae between the detector elements and can therefore be made higher. It should, however, be recognized that the invention can be used in combination with a conventional anti-scatter grid downstream of the lens as illustrated in FIG. 5; the lens will focus primary photons which would otherwise have been absorbed by the grid, hence increasing the geometric efficiency. Conversely, more aggressive grids which block more scattered photons could be used at maintained geometric efficiency.

The described setup further enables simultaneous acquisition of attenuation, phase-contrast and dark-field images of the object, which provide supplemental information on the morphology of the object for clinical imaging.

Figure 6:
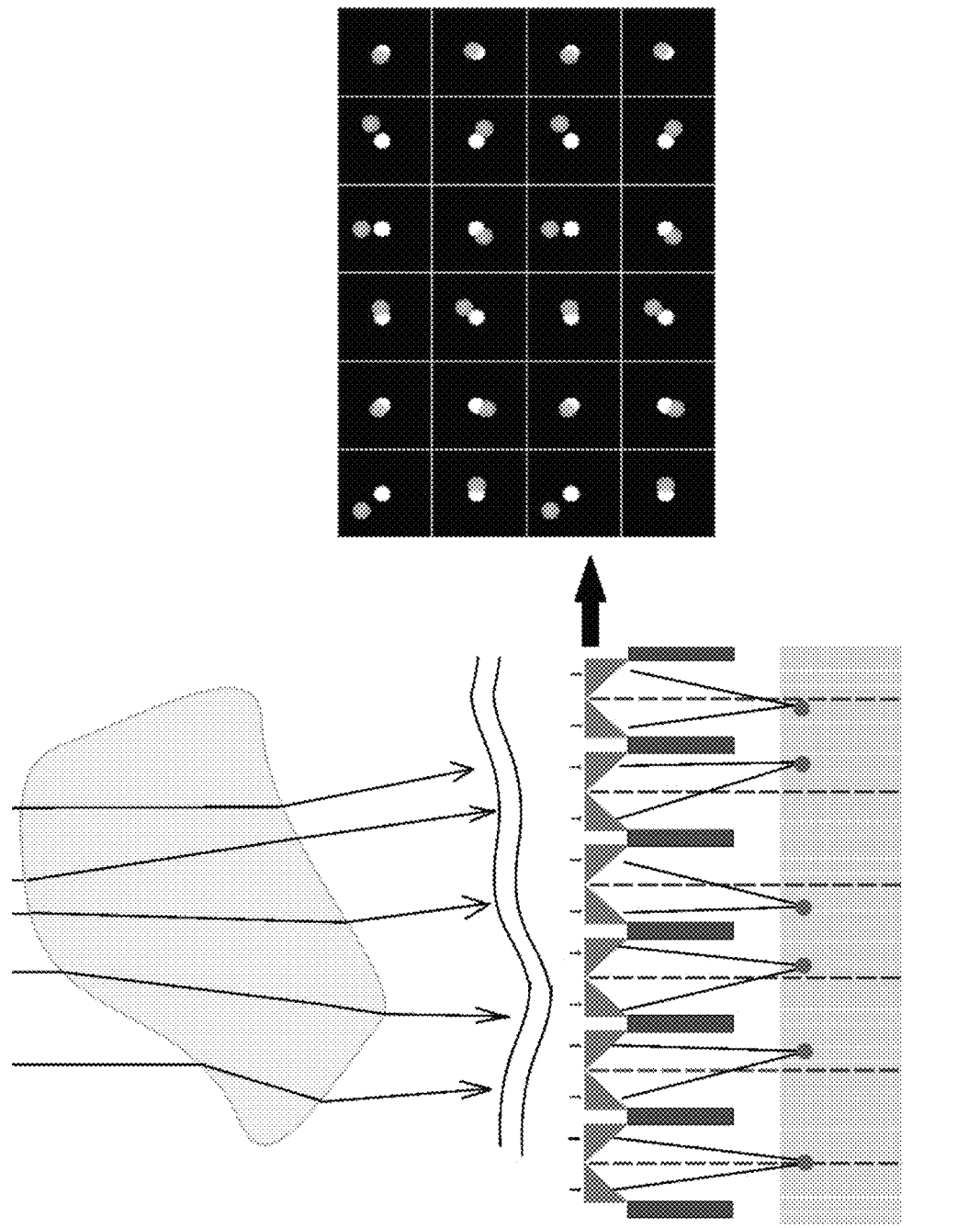
FIG. 6 is a schematic diagram illustrating an example of how wave front perturbations can manifest themselves and be measured by a detector combined with an in-line lens array.
Figure 7:
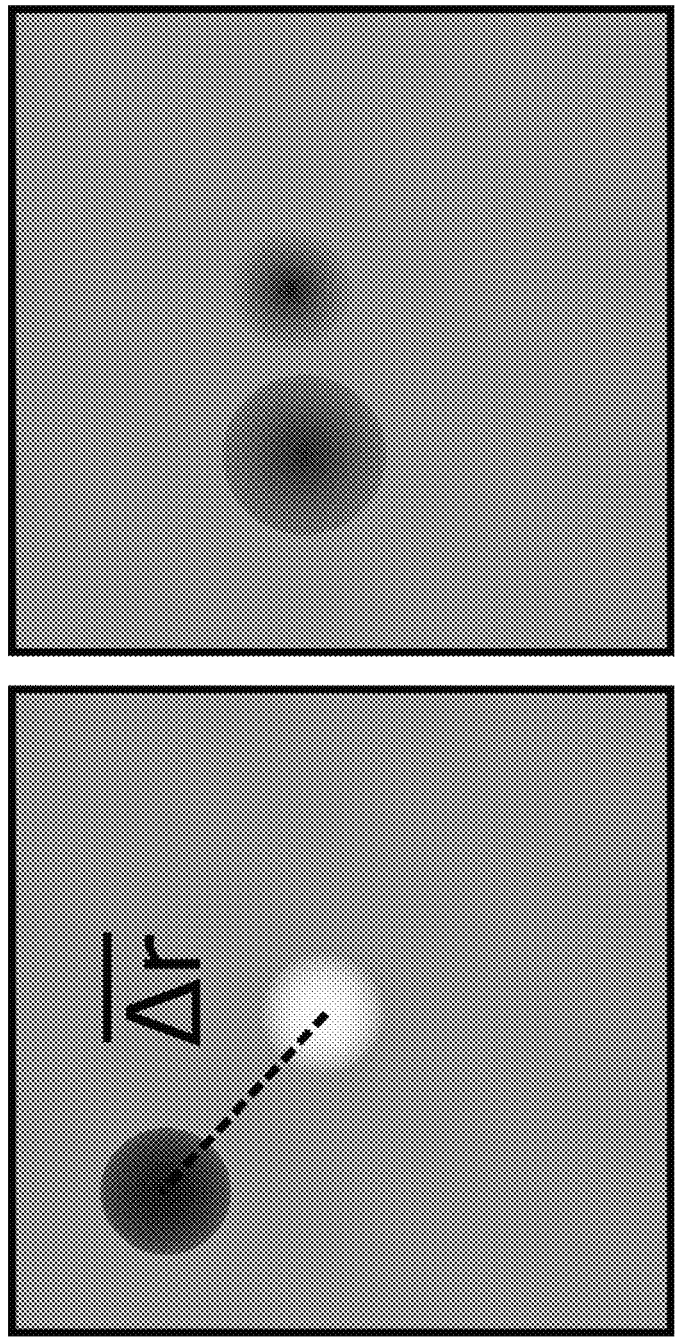
FIG. 7 is a schematic diagram illustrating an example of how the signal used to reconstruct an image is obtained from the intensity, spatial shift, and blur of the focal point.

The phase-contrast image is acquired as illustrated in FIG. 6 and FIG. 7. In FIG. 6, a lens array is positioned upstream of the detector and the lenses focus primary photons to an array of focal spots on the detector. A phase gradient at any point in the object shifts the location of the corresponding focal spot, which enables reconstruction of a differential phase-contrast image. If the lens array is focusing in two dimensions, the focal spot will move in both directions and an image of the two-dimensional phase gradient can be reconstructed. In FIG. 6 the nominal positions of the focal spots are depicted in white, while the observed spots are gray. The total phase shift, which is related to the real part of the refractive index ($\delta$), can be recovered by integration of the phase gradient. If projections are acquired from a range of angles around the object, a three-dimensional image of the real part of the refractive index ($\delta(x, y, z)$) can be reconstructed. In FIG. 7, a single focal spot from one lens is studied in closer detail. The spatial shift of the observed spot is indicative of the phase-gradient of the incoming wave front, as shown in FIG. 7a). FIG. 7b) gives a representative example of how the dark-field image signal is acquired, where the spread of the spot relates to the dark-field signal. Photons undergoing small-angle scattering in the object are not correlated, as opposed to phase-shift related deviations of the beam. Accordingly, scattered photons will not focus but will yield a diffuse broadening of the focal spot, which can be characterized using a high-resolution detector to reconstruct the dark-field image. A suitable parameter to characterize the broadening of the focal spot may be the full-width-at-half-maximum (FWHM) or, if a conventional anti-scatter grid is used to block wide-angle scatter, the total background signal.

As illustrated in FIG. 7, the attenuation image is acquired in tandem with the phase-contrast image and the dark-field image by measuring the total intensity of the detected beam, where counts outside of the detected focal spot can be rejected as scatter for the attenuation image, effectively reducing the scatter-to-primary ratio.

The described application of the lens array combined with a photon-counting detector to simultaneously acquire attenuation, phase-contrast and dark-field images has several advantages over grating-based phase-contrast geometries, including:

No translation of a detector grating is needed, which makes the setup less challenging from a mechanical perspective and reduces the acquisition time.

No detector grating is needed, which increases the dose efficiency substantially, typically by a factor of two, while absorption in the lens array is comparable to the phase grating in a grating-based setup.

The setup enables straight-forward measurement of two-dimensional phase gradients as lenses can be manufactured in two dimensions while gratings are intrinsically one-dimensional.

Temporal coherence is improved by the energy resolution and depth resolution of the detector, as described above.

Figure 8:
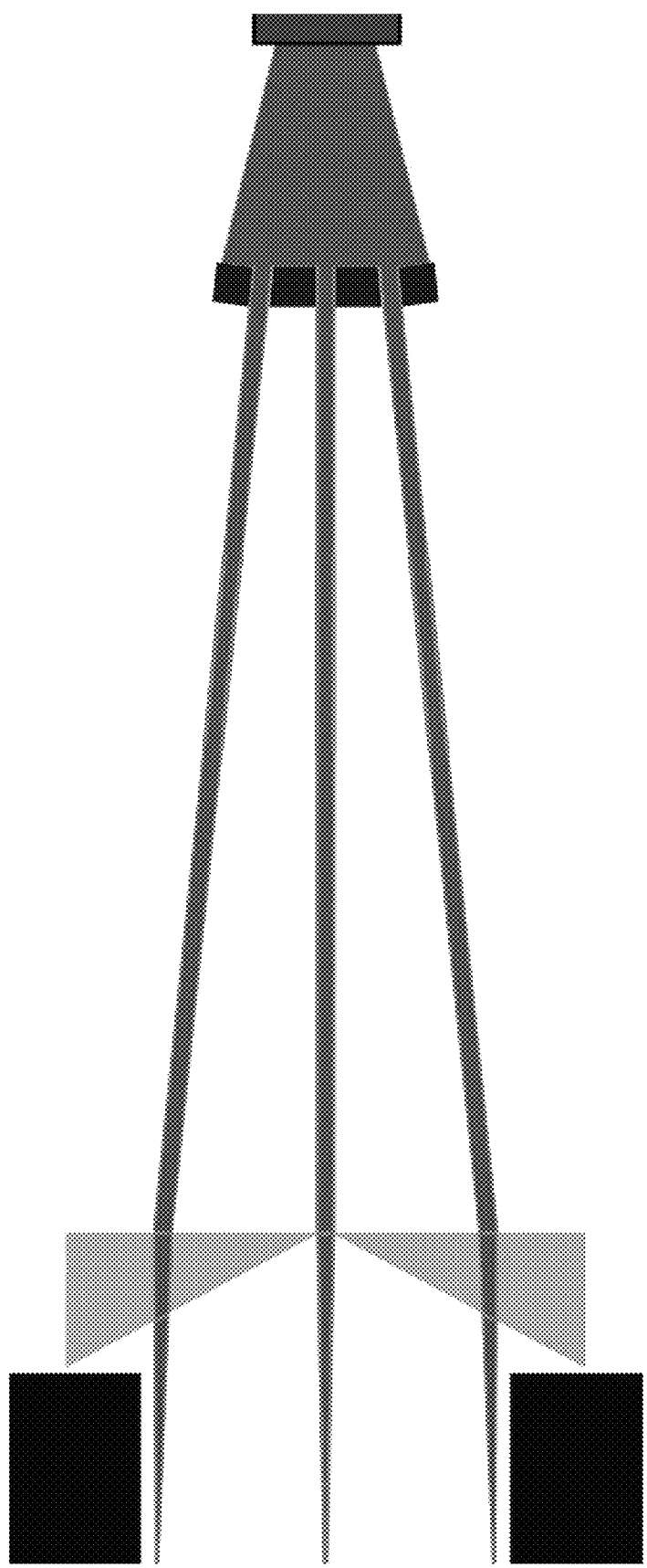
FIG. 8 is a schematic diagram illustrating an example of how the spatial coherence can be improved with pinholes situated in front of the source, so that each lens images several spots.

In order to improve spatial coherence, the arrangement for simultaneous acquisition of attenuation, phase-contrast and dark-field images can be combined with a grating (for one-dimensional lenses) or an array of pinholes (for two-dimensional lenses) placed in front of the source, as illustrated in FIG. 8. Each lens will then image an array of spots, each with higher coherence and smaller size compared to a setup without a grating/array of pinholes in front of the source.

The invention may use a high-resolution detector to measure the focal spot characteristics. Photon-counting detectors can be manufactured with exceptionally high resolution, but it should be noted that the resolution of the detector can be enhanced, if necessary, by several consecutive acquisitions while stepping a grating in front of the detector. The focal spot characteristics can also be measured to a precision greater than the size of the pixel pitch by, for example, a center-of-mass calculation of a focal spot peak that is distributed over several pixels. The variance of the centroid estimation can be reduced by combining the properties of an energy-resolving and depth-resolving detector. In a photon-limited system, the centroid error is proportional to the root-mean-square size of the spot in the direction transverse to the optical axis. The nominal width of the focal spot is related to the depth of interaction in the detector and the energy of the photon, and each count can be weighed to reduce the variance.

All of the mentioned configurations can be used for any medical x-ray imaging modality, such as for breast-imaging or computed tomography x-ray geometries.

For a better understanding, a more detailed disclosure will now be given with reference to non-limiting examples.

Chromatic Aberration

A major challenge when using x-ray optics in clinical x-ray imaging is the chromatic nature of the optics. Since state-of-the art clinical x-ray sources emit polychromatic x-ray spectra, it is desirable to address the chromaticity. By way of example, the focal length for an ideal refractive lens has a quadratic dependence on energy, and for a typical CT x-ray spectrum (tube voltage above 100 keV), the focal length can vary by more than one order of magnitude.

Figure 9:
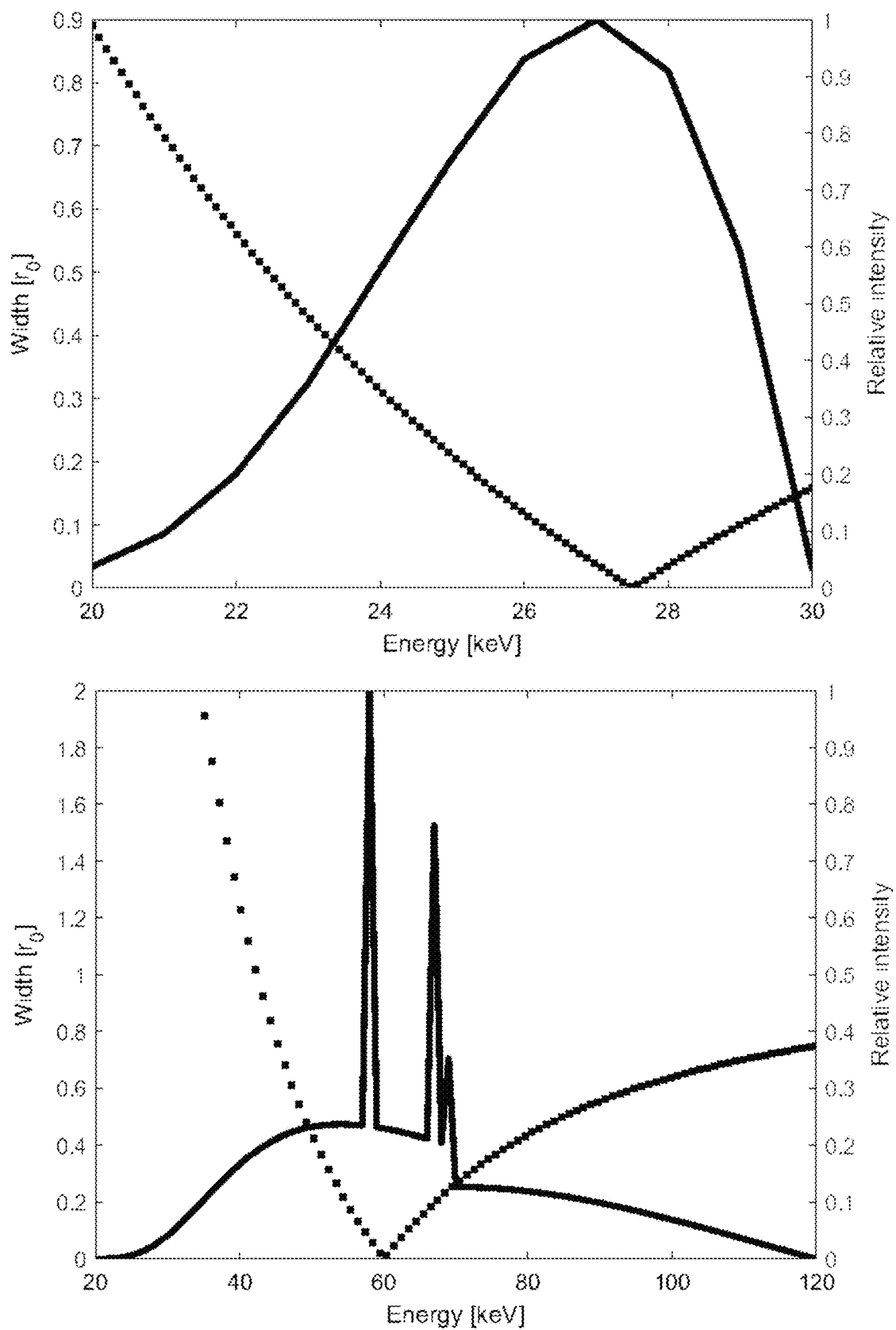
FIG. 9 is a schematic diagram illustrating an example of the width of a focal spot at a constant depth for several energies, overlaid with representative spectral intensities used in x-ray imaging.

The focal spot width at a depth t in the detector the detector follows (assuming geometrical optics and a thin lens) $r(t, E) = r_0|1-(t+LDD)/f(E)| = r_0|1-(t+LDD)/(K \times E^2)|$, where $r_0$ is the lens radius, LDD is the lens-to-detector distance, f (E) is the lens focal length, and E is the photon energy. The approximation is for a refractive x-ray lens with quadratic energy dependence and K is then a constant. At a plane t, the focus to a spot occurs only at an optimal energy $E^*(t) = \sqrt{(t+LDD)/K}$, while photons with lower and higher energies are not focused at this plane. The broadening of the focal spot at off-optimal energies is illustrated in FIG. 9 (dotted lines), superimposed on typical x-ray spectra (solid lines) for mammographic (FIG. 9, upper panel) and CT (FIG. 9, lower panel) imaging. The lens aperture is denoted $r_0$. The mammography illustration (FIG. 9, upper panel) has an optimal energy E* of 27.5 keV, and the CT illustration (FIG. 9, lower panel) has an optimal energy E* of 60 keV. For energies below the optimal energy E*, with the focal spot situated upstream of the detector, the beam area diverges rapidly at the detector plane, while for energies above the optimal energy E*, the width of the beam converges to the lens-aperture radius. Some x-ray optics, in particular diffractive x-ray optics, are only fully operational within a limited energy range and the blurring as a function of energy may be even stronger.

The present invention uses a photon-counting detector in combination with x-ray optics. As mentioned, with an energy-resolving photon-counting detector, each count is related to the incident photon energy. Hence, the focusing effect for energies near E* can be clearly resolved and delocalization from the optical axis can be more accurately estimated. In addition, photon-counting detectors enable volumetric resolution so that each count is related to the depth of interaction of the incident photon. The depth coordinate can be used to identify foci for energies not equal to E*, hence expanding the useful photon energy span and increasing efficiency. Further, photon-counting detectors have very low levels of electronic noise, which enables high spatial resolution (small detector elements) and detection even at very low dose levels.

Phase-Contrast Imaging

The stacked prism lens or another focusing lens can be used to estimate the differential phase shift of the object by measuring the refraction angle of a transmitted beam, and thereby provide phase-contrast information, as illustrated in FIG. 6 and FIG. 7. A lens focuses incident x-rays according to their incoming angle. Refraction of primary rays in the object manifests itself by a translation of the nominal focal spot along the focal plane. The translation can be detected with a detector having a size of the detector elements smaller than the aperture of the lens. Using lenses which focus in two dimensions, the refraction can be measured in two dimensions so that two separate orthogonal differential phase-contrast images are acquired. The phase signal is then proportional to $|\nabla \Phi| = \sqrt{(\partial \Phi(x,y)/\partial x)^2 + (\partial \Phi(x,y)/\partial y)^2}$, with the potential of, for instance, improving tumor visualization (3,29). Integration of the differential-phase contrast signal in one or two dimensions allows the total phase shift $\Phi(x, y)$ in the object to be estimated. With a rotating gantry and sufficient sampling angles, δ can then be acquired through backprojection.

As the angle of refraction is small, a high-resolution detector may be used to detect the translation of the focal spot, which is enabled by the photon-counting detector in the present invention. Moreover, energy and depth resolution of the photon-counting detector can be used for optimal weighting of photons, in particular to find photons of the optimal energy at a certain detector depth, hence compensating for lens chromaticity and the limited coherence of the source. Without energy- or depth-resolving capabilities, the focal spot translation may be shadowed by non-focused photons of other energies, as illustrated in FIG. 9, resulting in less efficient estimation of the phase-contrast signal.

The differential phase-contrast signal is provided by the deviation of the focal spot from its nominal position. The decrement δ decreases with energy approximately as $E^{-2}$, so the deviation is more subtle for high-energy photons. For a Shack-Hartmann wave-front sensor, a simple centroid has been shown to be the most accurate method to determine the center-of-mass of the focal spot, provided that there is no readout noise (30). The photon-counting detector has no, or negligible, readout noise, which is taken advantage of during signal processing and image formation.

With a focal spot that has a Gaussian distribution traverse to the primary beam, the photon noise limit of the centroid measurement error $\sigma_{err}$ (provided that there is no readout noise) is given as $\sigma_{err} = \sigma/\sqrt{N}$, where σ is the root-mean-square (rms) size of the focal spot and N is the number of photons. The rms of the focal spot varies both spatially and as a function of photon energy. Each registered count can be related to both the energy of the photon and the depth of interaction, so that the nominal rms at that depth and energy is known. Each photon count can then be weighed by, for instance, the inverse of the nominal rms focal spot width to reduce the centroid error. Due consideration is needed in cases where the focal spot is smaller than the pixel size and is only sampled by one pixel at any depth and/or energy (i.e., the focal spot only overlaps with a single pixel) as a centroid calculation in that case is limited by the pixel size.

The amount of counts in each small detector element, depth segment and energy bin may be low at realistic dose levels, and low levels of electronic noise may therefore be necessary to extract the signal.

The focal spot at the detector is essentially an image of the x-ray source and will therefore have a certain nominal width in the focal plane, determined by the source size and the relation between the source-to-lens and lens-to-detector distances. If the nominal width is too large, small transitions of the focal spot may be challenging to detect. However, in order to improve spatial coherence, the arrangement for phase-contrast imaging can be combined with a grating (for one-dimensional lenses) or an array of pinholes (for two-dimensional lenses) placed in front of the source, as illustrated in FIG. 8. Each lens will then image an array of spots, each with smaller size compared to a setup without a grating/array of pinholes in front of the source.

In addition, the refractive angle is energy dependent and measurement of the refraction as a function of energy with the photon-counting detector can potentially be used to quantitatively determine the material composition of the object. Further, the phase related component δ is inversely proportional to the energy squared, which causes the contrast-to-noise ratio (CNR) to vary with energy. The total CNR can therefore be increased by optimal weighting of the detected photons according to energy.

Two example configurations for differential phase-contrast imaging using the present invention have been evaluated with geometrical optics (raytracing) and will be described in the following section.

In the first configuration, a breast-imaging geometry was simulated, in which the source-to-detector-distance was 600 mm, and a single lens placed 100 mm upstream of the detector. The focal length of the lens was a nominal 100 mm at 20 keV, with quadratic energy dependence. The detector was a photon-counting silicon detector, of thickness 60 mm and with quadratic 50×50 µm² del size in the transverse plane. The tungsten-target x-ray source had a size of 0.2×0.2 mm² and was operated at a tube voltage of 32 kV. The lens diameter was 200 µm. An object was placed half-way between the source and the detector and induced a small refraction in a single plane. A realistic flux of 400 transmitted photons was simulated for each acquisition. The detector had a limited spectral resolution with two energy thresholds at 15 keV and 25 keV, which divided detected photons into two bins. All counts in the detector were summed up along the z axis, so no depth information was utilized in this simulation.

In the second configuration, a representative CT setup was simulated, in which the source-detector distance was 1010 mm, and a single lens was placed 100 mm upstream of the detector, with optimal energy for the lens being 40 keV. The tube voltage was 80 kV. The detector was a photon-counting silicon detector, of thickness 60 mm and with quadratic 100×100 µm² del size in the transverse plane. The lens diameter was 500 µm. 10,000 photons were simulated for each acquisition. In all other respects the simulation parameters were identical to the breast-imaging geometry.

Figure 10:
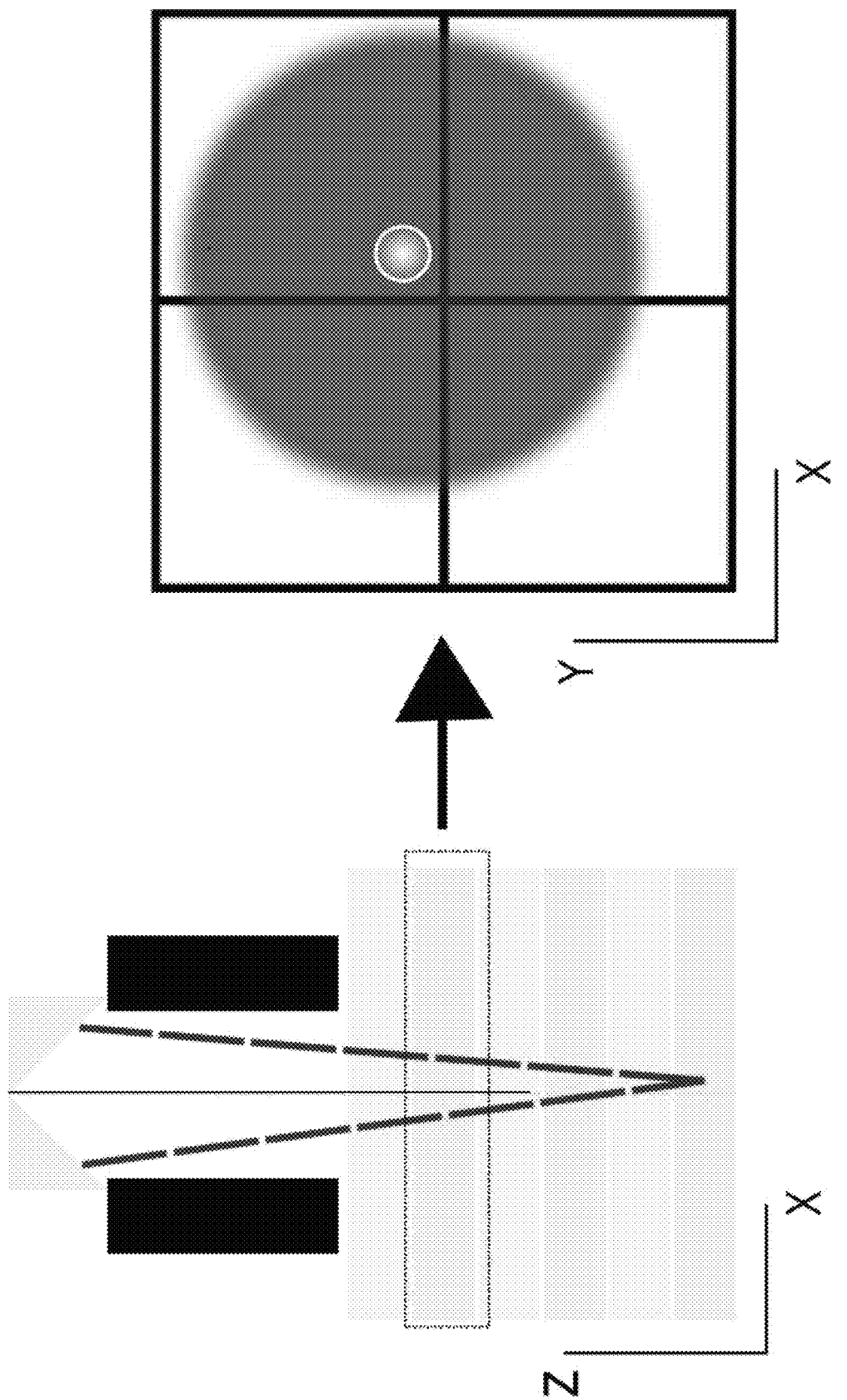
FIG. 10 is a schematic diagram illustrating an example of how the focal spot centroid can be determined at any depth in the detector.

The lens was aligned such that the optical axis coincided with the intersection between 4 adjacent pixels to maximize the sensitivity to focal-spot displacements. The deviation of the focal spot from its nominal position can be measured to a higher resolution than the detector pixels by a centroid calculation. The low level of electronic noise enabled by the photon-counting detector makes this calculation limited only by photon statistics and therefore optimal. For a Gaussian focal spot of size σ, the lower limit of the centroid measurement error is $\sigma_{err} = \sigma/\sqrt{N}$, where N is the number of counts (30). An example of a simple implementation of this method is given in FIG. 10. The left part of the image displays the optical axis parallel to the z axis and the depth resolution is provided by segmentation of the detector. The focusing is shifted from the optical axis. The right part of the figure shows the cross section at one depth in the detector. The centroid has a precision greater than the pixel resolution and can be calculated independently for all depths and energies in the detector. The counts can be weighted by their information content, for instance, by the inverse of the expected variance in the centroid measurement that results from a Gaussian focal spot if the nominal size is known for each depth and energy. The optical axis is ideally situated at the intersection between four adjacent pixels for greatest sensitivity to small translations of the focal spot.

Figure 11:
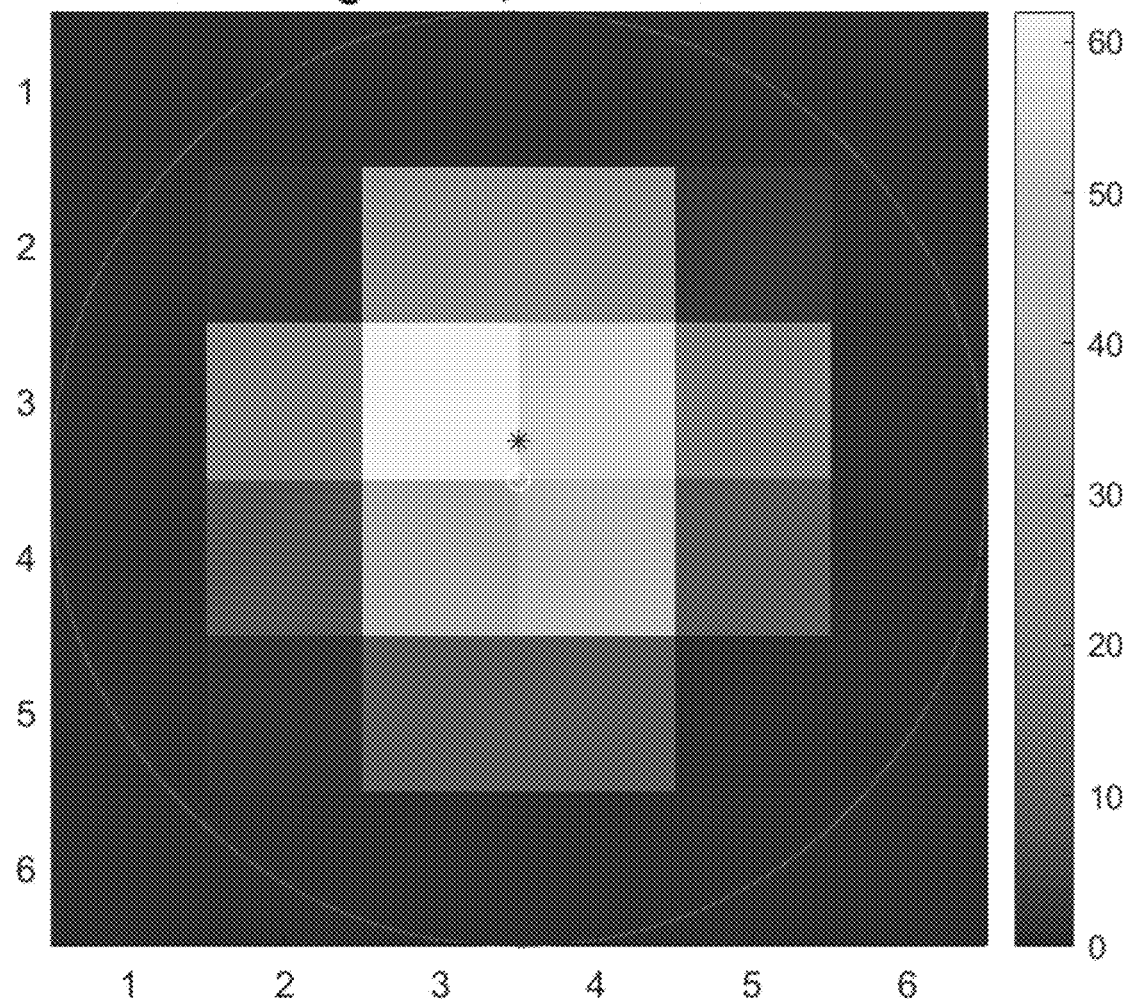
FIG. 11 is an image obtained from a simulated setup, demonstrating detection of the focal spot translation from a centroid.
Figure 12:
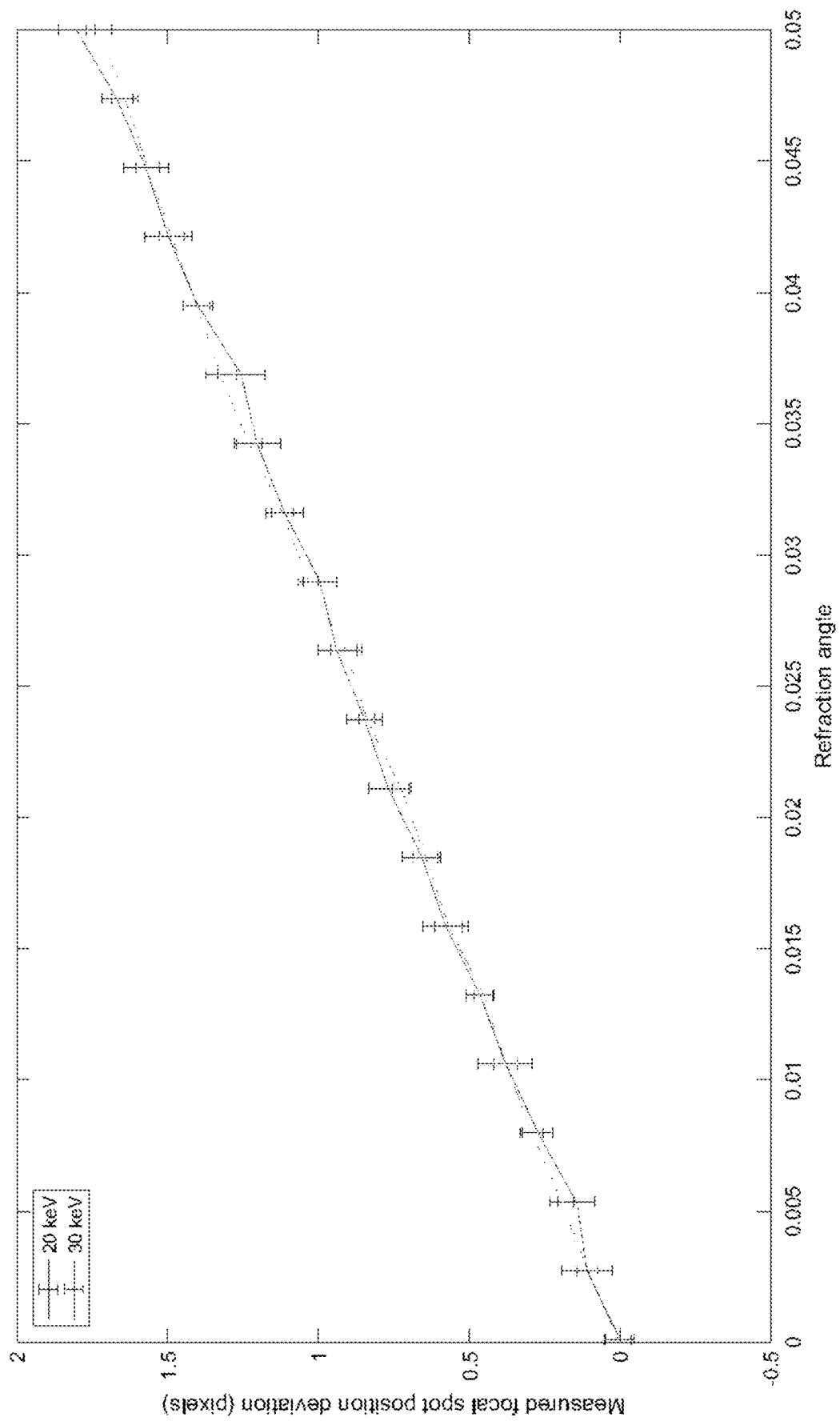
FIG. 12 is a representative plot demonstrating the translation of the detected focal point due to refraction in the imaged object in a simulated breast imaging geometry.
Figure 13:
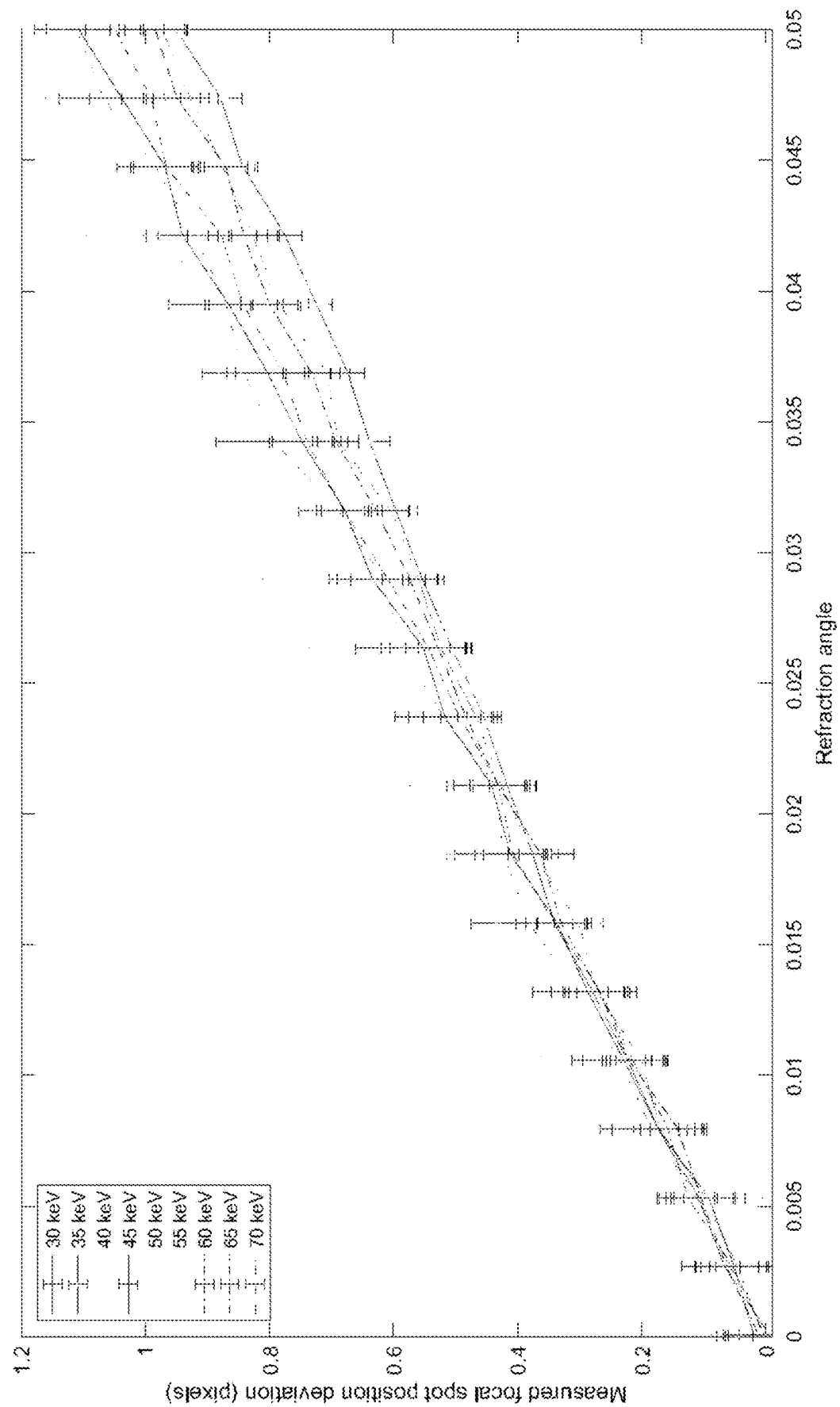
FIG. 13 is a representative plot demonstrating the translation of the detected focal point due to refraction in the imaged object in a simulated computed tomography geometry.

The results of the simulations are shown in FIG. 11, 12, 13. In FIG. 11, the detected counts from a lens-detector element is shown for the breast-imaging setup, where the source-detector-distance was 60 cm, with a tube voltage of 32 kV and 50 µm pixel size. The white circle indicates the optical axis of the lens in the x-y plane, indicates and the red star indicates the calculated center of mass of the detected intensity distribution in the x-y plane. The deviation in they direction is caused by object refraction. The simulation was repeated 20 times for 20 different refractive angles in the object, with results shown in FIG. 12 for the breast-imaging geometry and FIG. 13 for the CT-geometry. The standard deviation is shown with error bars in the plots. The displacement of the focal spot is linear in relation to the refraction angle ($R^2=0.9992$ for the 30 keV plot in FIG. 12).

Refraction angles of less than 0.0027 deg could be measured accurately with each energy bin (coefficient of variation 0.343). In practice, each lens-detector unit is preferably calibrated by a flat-field acquisition to determine the optical axis and nominal point-spread function of the lens. Acquired images are then compared to this calibration, so that a detected deviation of the focal point with respect to the calibration is equivalent to sampling $\nabla\Phi$.

The chief advantage of this method for sampling the phase-aberration of the wavefront compared to existing Talbot-Lau methods include the mechanical simplicity of the setup and the expected low acquisition time. Talbot-Lau interferometers typically require translation of the analyzer grating. An abdominal projection of a pig with a Talbot-Lau interferometer had a 40 second scan time to acquire a single projection (10). To adequately sample the wavefront in a rotating CT gantry for tomographic reconstruction with just 90 projection angles (a very low number compared to state-of-the-art CT) would then at this take an hour. For comparison, gantries in state-of-the-art CTs today can rotate at several revolutions per second. In principle, the lens-array configuration we propose can be used to acquire phase-contrast and dark-field images in a rotating gantry at the same sampling frequency as with state-of-the-art CTs in clinical use today.

X-ray sources used in clinically today have a finite bandwidth and finite focal spot. The latter leads to spatial coherence being compromised. For the proposed imaging techniques with the lens-array, some imaging tasks might advantageously use spatial filtering to increase spatial coherence. This can be done by placing either a grating or pinholes downstream of the source. An incoherently illuminated pinhole with aperture radius a displays a normalized degree of coherence described by van Cittert-Zernike's theorem as $$\mu_{OP}(\theta) = \exp\left(-i\frac{kz\theta^2}{2}\right)\frac{2J_1(ka\theta)}{ka\theta},$$

where k is the wavenumber and $J_1$ is a Bessel function of the first kind of order one, and θ is the angle from the z-axis (6). The spacing between pinhole/grating aperture, and the size of the aperture could be varied to suit the configuration and imaging task. Two-dimensional lenses in the lens-array may preferentially use a pinhole array, while a grating may offer a better trade-off between coherence and flux for one dimensional lenses.

Each lens in the lens-array would image a number of spots, each exhibiting greater spatial coherence and smaller size compared to the case without spatial filtering, which, if individually resolved by the high-resolution photon-counting detector, would offer denser sampling of the phase gradient. The trade-off between spatial coherence and photon flux would need to be evaluated for each imaging task and could depend on many factors such as the geometry of the setup, tube voltage, detector resolution and the characteristics of the pathology being investigated.

To resolve the focal spots imaged by the lenses, a high-resolution detector may be used. However, some refraction processes may surpass the sensitivity of the detector and the resolution could be increased by placing an absorbing grating in front of the detector. The grating period could be adapted for the imaging task. The grating could be translated across the detector stepwise over an entire grating period, in analogue to phase-stepping in a GBI setup. The trade-off Dark-Field Imaging Small-angle scattering in the object will result in broadening of the focal spot because scattered photons will have a random component in their incidence angles and will therefore not be uniformly focused towards a point. Photons undergoing small-angle scattering in the object are not correlated, as opposed to phase-shift related deviations of the beam. Accordingly, scattered photons will not focus but will yield a diffuse broadening of the focal spot, which can be characterized using a high-resolution detector.

One method to quantify the broadening of the focal spot is to measure the full width at half maximum (FWHM). Another method to determine the dark-field signal is to measure the background noise in the area outside the focal spot; with an anti-scatter grid to remove most incoherent scatter, the background counts outside of the focal spot is indicative of the total amplitude of small-angle scatter.

As mentioned, the relative amount of counts outside of the focal spot may be low near the optimal energy of the lens and low levels of electronic noise may therefore be necessary to extract the signal, which is enabled by the photon-counting detector in the present invention. Moreover, energy and depth resolution of the photon-counting detector can be used to discriminate against primary (non-scattered) photons outside of the optimal energy at a certain detector depth. Without energy- or depth-resolving capabilities, the focal spot blur caused by small-angle scattering will be polluted by non-focused primary photons, as illustrated in FIG. 9, resulting in less efficient estimation of the dark-field signal.

As for phase-contrast imaging, the detected focal spot will have a certain nominal width in the focal plane, determined by the source size and the relation between the source-to-lens and lens-to-detector distances. If the nominal width is too large, the blur of the focal spot caused by small-angle scattering may be challenging to detect. However, a grating (for one-dimensional lenses) or an array of pinholes (for two-dimensional lenses), as illustrated in FIG. 8, can be placed in front of the source to improve spatial coherence. Each lens will then image an array of spots, each with smaller size compared to a setup without a grating/array of pinholes in front of the source.

The detected focal spot might be blurred owing to several other factors, including the point-spread function of the lens, which might range from 150 nm to 10 µm FWHM in realistic setups. Similar to what was described for phase-contrast imaging above, a calibration procedure using a flat-field acquisition might therefore be preferable in order to be able to deconvolve the detected signal with the point-spread function.

The broadening of the beam caused by small-angle scattering is related through a line integral to the linear diffusion coefficient, according to Eq. (3). This relationship allows for volumetric reconstruction of the linear diffusion coefficient from an angular range of projections, for both tomosynthesis and CT applications. Some crystalline materials, such as some bones, may have scattering asymmetry depending on the orientation of the incident beam, which may have to be taken into account for tomographic reconstruction. This angular dependency need not be a disadvantage as directional dark-field imaging can be used to determine the local angle and degree of orientation of bone (11).

As for phase-contrast imaging, the cross section for small-angle scattering is energy dependent and measurement of the dark-field signal as a function of energy with the photon-counting detector can potentially be used to quantatively determine the materials composition of the object. Further, the cross section of coherent scattering relative the Compton (incoherent) cross section decreases at a rate approximately proportional to $E^{-1.6}$ for water; the relative contributions to the total cross sections are equal at about 13 keV, while at 100 keV the relative contribution of coherent scattering is only about 3% (31). This relation causes the contrast-to-noise ratio (CNR) to vary with energy and the total CNR can be increased by optimal weighting of the detected photons according to energy.

Anti-Scatter

Similar to the ability of the invention to detect small-angle scattering, it can also be employed to reject large-angle Compton scattering, which deteriorates the CNR in x-ray imaging.

Primary (non-scattered and forward-scattered) photons are nearly parallel when reaching the detector with only small deviations from the size of the x-ray source and from small angles of refraction in the object. Photons undergoing small-angle scattering are also nearly parallel, in comparison to photons undergoing Compton scattering, which exhibit a wide angular distribution. Primary photons and photons undergoing small-angle scattering are therefore focused by the array of x-ray lenses to a relatively small focal spot, which can be discriminated from the large spread of Compton scattered photons.

By way of example, if the configuration is such that the lens aperture spans at least three detector pixels, primary and small-angle-scattered photons are focused towards the central pixel, while Compton-scattered photons cover more than one pixel and can thus be separated. These scattered photons could not be separated if primary photons are transmitted without refraction through the lens. This basic idea can readily be extended to more advanced schemes for separation, such as a more exact measurement of the focal spot width, quantified, for instance, by the FWHM as for the dark-field configuration above. The high detector resolution for this configuration is enabled by the photon-counting detector, and the low levels of electronic noise in this type of detector facilitates separation of the focal spot peak from the background. As for phase-contrast and dark-field imaging, energy and depth resolution of the detector can greatly improve the performance by compensating for the chromatic behavior of the lens. In addition, the relative amount of Compton scattering is energy dependent and more stringent separation can be applied in energy regions where Compton scattering dominates.

The lens array could also be implemented in conjunction with a conventional anti-scatter grid to separate primary from scattered photons. An anti-scatter grid has, by necessity, a certain width transverse to the primary beam axis and will therefore shadow parts of the detector area and consequently reduce the geometric efficiency. If the lens-array is placed upstream of the anti-scatter grid, primary photons which would otherwise have been shadowed by the grid are focused to pass through the grid lamella. This configuration is demonstrated in FIG. 5; FIG. 5a) shows primary photons striking the grid, and FIG. 5b) illustrates how photons can be focused to hit the detector. Scatter rejection is demonstrated by comparing FIG. 5b) and FIG. 5a); parallel photons are focused to a spot while scattered photons with a wide distribution of incident angles are not focused. In FIG. 5b), the scattered photon interacting with the detector can be rejected because it is not detected at the location of the focal spot.

FIG. 5c) demonstrates how the scatter-to-primary ratio can be improved at maintained geometric efficiency by allowing for more aggressive anti-scatter grid designs with wider base in the direction orthogonal to the primary photons. Similarly, manufacturing tolerances for anti-scatter grids can be made less stringent, for instance, the straightness of the grid becomes less critical if the grid does not shadow the detector and the grid can be made longer in the direction parallel to the photons at maintained geometric efficiency.

Figure 4:
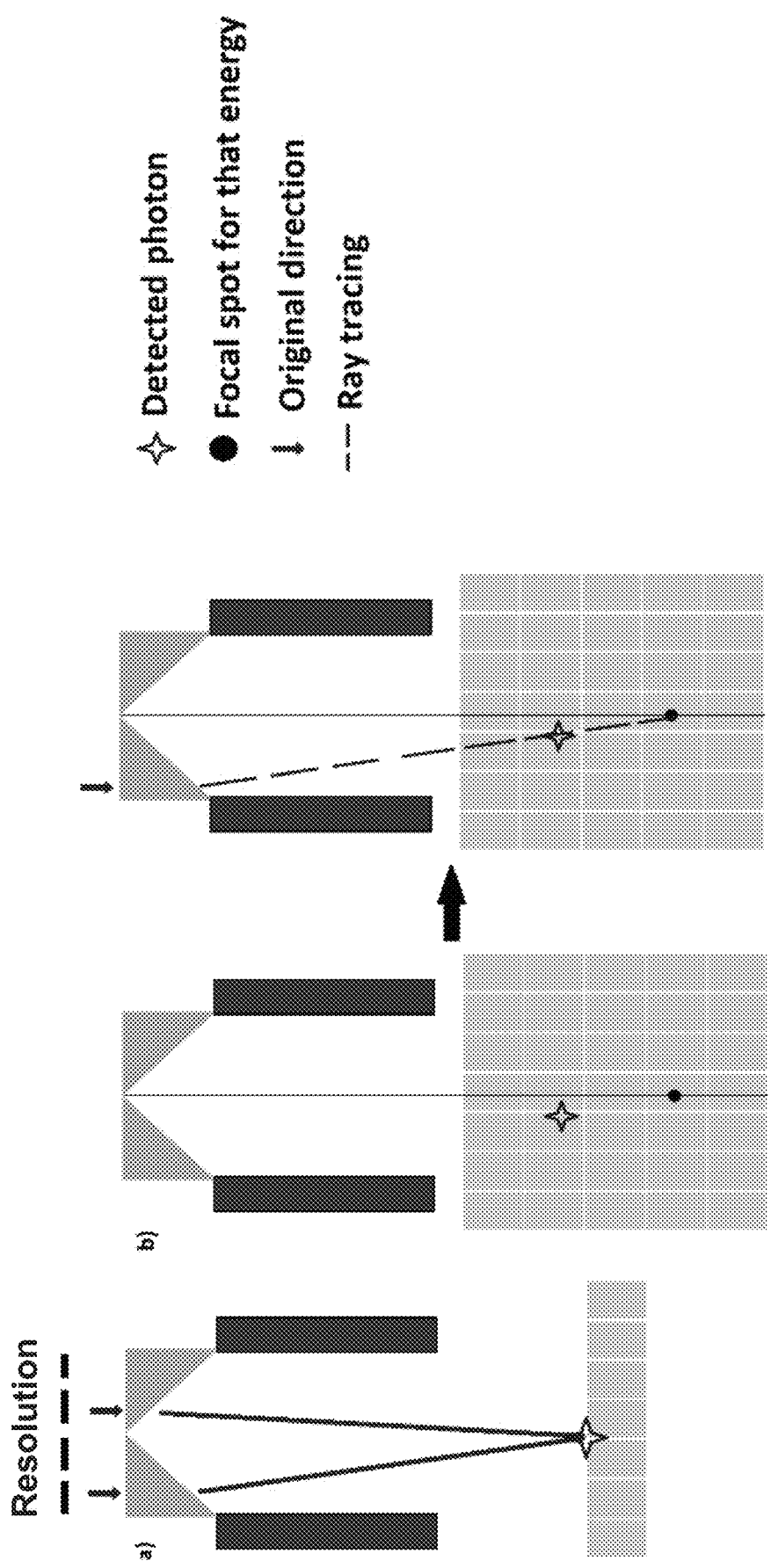
FIG. 4 is a schematic diagram illustrating an example in which the transverse spatial resolution that has been lost when focusing with a lens can be recovered with a combination of a depth- and energy-resolving detector and ray-tracing.

The spatial resolution of the described configuration for scatter rejection is limited by the aperture of each lens in the array and not by the detector elements, which are generally smaller. As shown schematically in FIG. 4, the narrower the focusing, more resolution is lost and the ability to resolve the original transverse location of the photons is reduced accordingly. However, a raytracing method to recover spatial information, i.e. the position at which the primary photon entered the lens aperture, is enabled by a photon-counting detector, which has both energy and depth resolution. For a given recorded energy, the focal length of the lens is known, and the nominal focal spot position can be calculated. A line drawn in three dimensions through the recorded count position and the nominal focal spot position intersects the point where the photon entered the lens aperture. This method is illustrated in FIG. 4. In practice, more sophisticated statistical methods would preferentially be employed. The gain in spatial resolution is limited by factors such as source size, imperfect focusing in the lens, limited energy and spatial resolution of the detector, and refraction of primary photons in the object.

Figure 14:
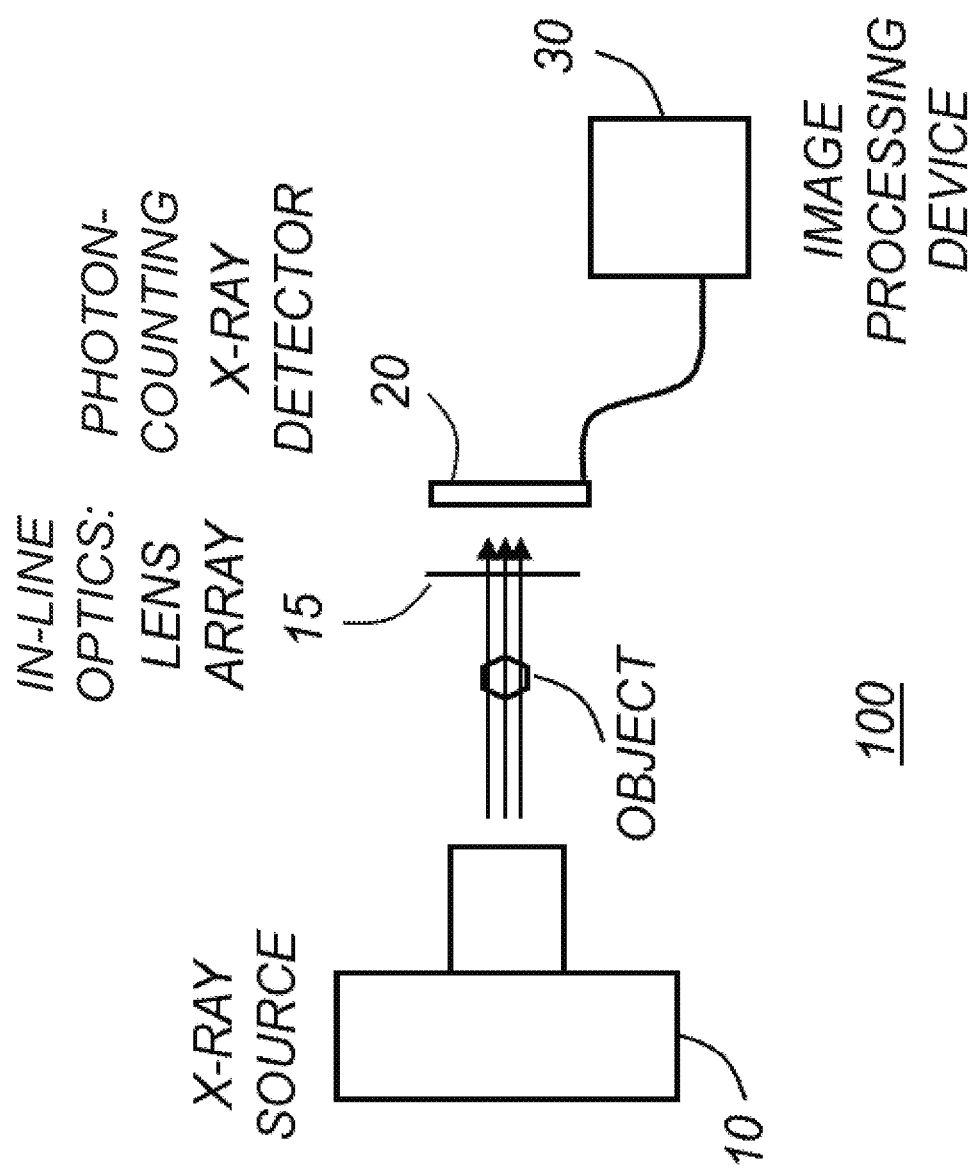
FIG. 14 is a schematic x-ray imaging system. It can be noted that the lens array may be placed between the object and the detector, but it may also be placed between the source and the object.

FIG. 14 is a schematic diagram illustrating an example of an x-ray imaging system. In this non-limiting example, the x-ray imaging system 100 basically comprises an x-ray source 10, x-ray optics such as a lens array 15, an x-ray detector 20 and an associated processing device 30. In general, the x-ray detector system 20 is configured for registering radiation from the x-ray source 10 that have passed an object or subject or part thereof and focused by the lens array 15 optics. As indicated, the lens array 15 may be placed between the object and the detector, but it may also be placed between the source and the object. The x-ray detector 20 is connectable to the processing device 30 via suitable analog processing and read-out electronics (which may be integrated in the x-ray detector system 20) to enable computations, post-processing and/or pre-processing, and/or image processing and/or image reconstruction by the processing device 30. It will be appreciated that the methods and devices described herein can be combined and re-arranged in a variety of ways.

For example, specific functions may be implemented in hardware, or in software for execution by suitable processing circuitry, or a combination thereof.

The steps, functions, procedures, modules and/or blocks described herein may be implemented in hardware using any conventional technology, such as semiconductor technology, discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

By way of example, the arrangement and/or the overall x-ray imaging system may include processing circuitry configured to perform the signal and/or data processing functions described herein.

Figure 15:
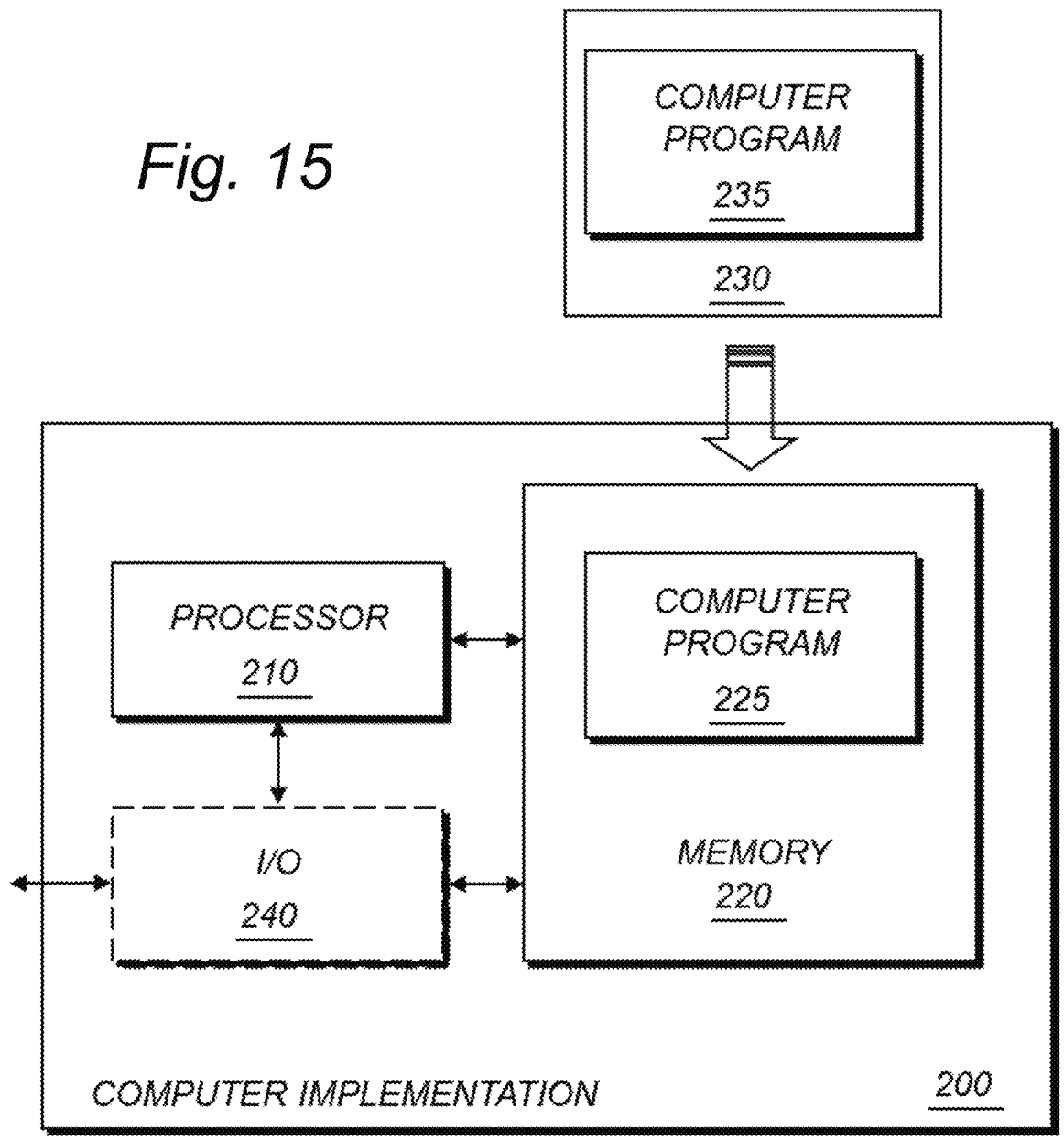
FIG. 15 illustrates an example of a schematic computer implementation for enabling computations and/or methods and/or procedures or parts thereof as described herein.

FIG. 15 is a schematic diagram illustrating an example of a computer implementation according to an embodiment. In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

The method flows presented herein may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively, it is possibly to realize the modules predominantly by hardware modules, or alternatively by hardware. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

REFERENCES

1 Zanette I, Zhou T, Burvall A, Lundström U, Larsson D H, Zdora M, et al. Speckle-based x-ray phase-contrast and dark-field imaging with a laboratory source. Phys Rev Lett. 2014; 112(25):1-5.
2. Bech M, Tapfer A, Velroyen A, Yaroshenko A, Pauwels B, Hostens J, et al. In-vivo dark-field and phase-contrast x-ray imaging. Sci Rep. 2013; 3:10-2.
3 Twengström W. High-resolution biomedical phase-contrast tomography. 2018.
4. Bech M, Bunk O, Donath T, Feidenhans'l R, David C, Pfeiffer F. Quantitative x-ray dark-field computed tomography. Phys Med Biol. 2010; 55(18):5529-39.
5. Schlomka J-P, Harding A, van Stevendaal U, Grass M, Harding GL. Coherent scatter computed tomography: a novel medical imaging technique. Proc. SPIE 5030, Medical Imaging 2003: Physics of Medical Imaging. 2003.
6. Attwood D, Sakdinawat A. X-Rays and Extreme Ultraviolet Radiation. In: X-Rays and Extreme Ultraviolet Radiation. 2016. p. 67-69, 134, 469, 578-591.
7 Pfeiffer F, Weitkamp T, Bunk O, David C. Phase retrieval and differential phase-contrast imaging with low-brilliance X-ray sources. Nat Phys. 2006; 2(4):258-61.
8. Scherer KH. Grating-Based X-Ray Phase-Contrast Mammography. Springer. 2016.
9. Michel T, Rieger J, Anton G, Bayer F, Beckmann M W, Durst J, et al. On a dark-field signal generated by micrometer-sized calcifications in phase-contrast mammography. Phys Med Biol. 2013; 58(8):2713-32.
10. Gromann L B, De Marco F, Willer K, Noël P B, Scherer K, Renger B, et al. In-vivo X-ray Dark-Field Chest Radiography of a Pig. Sci Rep. 2017; 7(1):1-7.
11. Jensen T H, Bech M, Bunk O, Donath T, David C, Feidenhans'L R, et al. Directional x-ray dark-field imaging. Phys Med Biol. 2010; 55(12):3317-23.
12. Hubbell JH. Summary of existing information on the incoherent scattering of photons, particularly on the validity of the use of the incoherent scattering function. Radiat Phys Chem. 1997; 50(1):113-124.
13. Schlomka J-P, Delfs J, Barschdorf H, Thran A, van Stevendaal U. Experimental feasibility study of energy-resolved fan-beam coherent scatter computed tomography. Proc. SPIE 5535, Developments in X-Ray Tomography IV. 2004.
14. Cozzini C, Harding G, Edic P, Beque D, Kosciesza D, Du Y, et al. Energy dispersive X-ray diffraction spectral resolution considerations for security screening applications. IEEE Nuclear Science Symposuim & Medical Imaging Conference, pp. 3873-3876.2010.
15. Nisar M, Johns PC. Coherent scatter x-ray imaging of plastic/water phantoms. Proc. SPIE 5578, Photonics North 2004: Photonic Applications in Astronomy, Biomedicine, Imaging, Materials Processing, and Education. 2004.
16. Snigirev A, Kohn V, Snigireva I, Lengeler B. A compound refractive lens for focusing high-energy X-rays. Nature. 1996; 384:49-51.
17. Snigirev A, Snigireva I, Grigoriev M, Yunkin V, Di Michiel M, Vaughan G, et al. High energy X-ray nanofocusing by silicon planar lenses. Journal of Physics: Conference Series. Vol. 186. No. 1. IOP Publishing, 2009.
18. Fredenberg E, Cederström B, Åslund M, Ribbing C, Danielsson M. A Tunable Energy Filter for Medical X-Ray Imaging. X-Ray Opt Instrum. 2008.
19. Fredenberg E, Cederström B, Nillius P, Ribbing C, Karlsson S, Danielsson M. A low-absorption x-ray energy filter for small-scale applications. Opt Express. 2009; 17(14):11388-98.
20. Nillius P, Karlsson S, Cederström B, Fredenberg E, Danielsson M. Large-aperture focusing of high-energy x-rays with a rolled polyimide film. Opt Lett. 2011; 36(4):555-7.
21. Mi W, Karlsson S, Holmberg A, Danielsson M, Nillius P. Fabrication of circular sawtooth gratings using focused UV lithography. J Micromechanics Microengineering. 2016; 26(3).
22. Karlsson S. Approach and device for focusing x-rays. U.S. Pat. No. 7,742,574B2.
23. Mi, W, Nillius, P, Pearce, M and Danielsson, M. A stacked prism lens concept for next-generation hard X-ray telescopes. Nature Astronomy. 2019.
24. Fredenberg E, Cederström B, Åslund M, Nillius P, Danielsson M. An efficient pre-object collimator based on an x-ray lens. Med Phys. 2009; 36(2):626-33.
25. Anton G, Preusche O. X-ray device. US2015/0055744A1.
26. Heid O. Bildgebendes system and verfahren zur bildgebung. WO2014/187588A1.
27. Atsushi O, Yasuaki T, Akira Y. X-ray imaging system and x-ray imaging method. JP2008200357A.
28. Persson M. Spectral Computed Tomography with a Photon-Counting Silicon-Strip Detector. PhD Thesis, KTH Royal Institute of Technology. 2016.
29. Pagot E, Fiedler S, Cloetens P, Bravin A, Coan P, Fezzaa K, et al. Quantitative comparison between two phase contrast techniques: diffraction enhanced imaging and phase propagation imaging. Phys Med Biol. 2005; 50(4): 709-24.
30. Thomas S. Optimized centroid computing in a Shack-Hartmann sensor. Adv Adapt Opt. 2004; 5490:1238.
31. Berger M J, Hubbell J H, Seltzer S M, Coursey J S, Zucker D S. XCOM: Photon Cross Section Database. Gaithersburg, Md.: National Institute of Standards and Technology (NIST); 2009. version 1.4. Available from: http://physics.nist.gov/xcom
32. Vedantham; Srinivasan. Apparatus and method for x-ray phase contrast imaging. US 2017/0219503

The invention claimed is:

1. An arrangement comprising an x-ray detector arranged in conjunction with in-line x-ray focusing optics configured for manipulation of x-rays in medical transmission radiography, wherein the in-line x-ray optics comprises an array of lenses, in which the lenses cover parts of, or the entire, field of view, and in which the x-ray detector is a photon-counting detector,
wherein the x-ray detector is a depth-resolving detector and chromatic aberration of the lens array and/or limited coherence of the source is compensated for by depth resolution or volumetric resolution in the x-ray detector.

2. The arrangement according to claim 1, which is configured to separate primary photons from scattered photons such that primary photons, which are parallel or near parallel, are concentrated to a focus, whereas scattered photons with a wider angular distribution are not concentrated to a focus.

3. The arrangement according to claim 2, in which the x-ray detector is a pixelated detector and the separation between primary and scattered photons is conducted with the pixelated detector, said detector having two or more pixels covering each lens in the lens array.

4. The arrangement according to claim 2, in which scattered photons are blocked by means of an anti-scatter grid in addition to the lens array.

5. The arrangement according to claim 2, in which scattered photons are blocked by means of a pin hole or a slit upstream of the x-ray detector.

6. The arrangement according to claim 1, in which the arrangement is configured for operation with raytracing methods used in conjunction with energy and/or depth resolution in the x-ray detector to increase spatial resolution of the arrangement.

7. The arrangement according to claim 1, in which the arrangement is configured to estimate or enable estimation of the local phase gradient of the imaged object in one or two dimensions at each lens from the detected location of the focal spot relative to the optical axis of the lens.

8. The arrangement according to claim 1, in which the arrangement is configured to obtain or enable the obtaining of information on small-angle scattering in the object from the broadening of the focal spot or from the total signal outside of the focal spot peak.

9. The arrangement according to claim 7, in which the arrangement is configured to determine or enable determination of the location and/or size of the focal spot of each lens by scanning a grating or a number of pin holes in front of the x-ray detector.

10. The arrangement according to claim 7, in which the x-ray detector is a high-resolution detector and the arrangement is configured to determine or enable determination of the location and/or size of the focal spot of each lens by detecting the signal with the high-resolution detector, said detector having a resolution higher than the deviation of the focal spot from the focal spot's nominal size and position.

11. The arrangement according to claim 7, in which the arrangement is configured to determine or enable determination of the location and/or size of the focal spot to a higher resolution than the detector, where two or more detector elements of the x-ray detector sample the distribution of focused photons reaching the x-ray detector.

12. The arrangement according to claim 7, in which the arrangement comprises a grating or a number of pin holes placed in front of the source, such that each lens in the lens array is operable for imaging a number of spots.

13. The arrangement according to claim 1, which is configured for breast imaging.

14. The arrangement according to claim 1, which is configured for computed tomography.

15. The arrangement according to claim 1, which is configured for fluoroscopic imaging.

16. The arrangement according to claim 1, which is configured to simultaneously acquire at least two of transmission, phase-contrast and dark-field images.

17. The arrangement according to claim 1, in which the lens array focuses in one dimension so that the focus is a line.

18. The arrangement according to claim 1, in which the lens array focuses in two dimensions so that the focus is a spot.

19. The arrangement according to claim 1, in which the lens array is placed between the object and the x-ray detector.

20. The arrangement according to claim 1, in which the lens array is placed between the source and the object.

21. The arrangement according to claim 1, in which the energy and/or depth resolution of the photon-counting detector is used to sort photons into categories, which are treated differently depending on the energy and/or depth of interaction.

22. The arrangement according to claim 21, in which the energy and/or depth resolution of the photon-counting detector is used for weighting of photons such that photons carrying more information are assigned a higher weight compared to photons carrying less information.

23. The arrangement according to claim 1, in which the arrangement comprises processing circuitry configured to perform signal and/or data processing.

24. An x-ray imaging system and/or a system for medical x-ray imaging comprising an arrangement according to claim 1.

25. The x-ray imaging system of claim 24, in which the x-ray detector is an energy-resolving detector and the system is configured to decompose the focus into energy-resolved components.

26. The x-ray imaging system of claim 24, in which the x-ray detector is a depth-resolving detector and the x-ray imaging system is configured to compensate for the chromatic aberration by using the depth resolution or volumetric resolution of the x-ray detector, either independently or in conjunction with energy resolution of the x-ray detector.

27. The x-ray imaging system of claim 24, in which the x-ray imaging system is configured for performing raytracing in conjunction with energy and/or depth resolution in the detector to increase spatial resolution.

28. The x-ray imaging system of claim 24, in which the x-ray imaging system comprises processing circuitry configured to perform signal and/or data processing.

29. The arrangement according to claim 1, wherein the x-ray detector is an energy-resolving detector and chromatic aberration of the lens array and/or limited coherence of the source is compensated for by the energy resolution of the energy-resolving detector.

* * * * *